US007122652B1

(12) United States Patent
Wojnowski et al.

(10) Patent No.: US 7,122,652 B1
(45) Date of Patent: Oct. 17, 2006

(54) POLYMORPHISMS IN THE HUMAN HPXR GENE AND THEIR USE DIAGNOSTIC AND THERAPEUTIC APPLICATIONS

(76) Inventors: Leszek Wojnowski, Ebenauer Strasse 9, Munich (DE) 80637; Elisabeth Hustert, Geschwister-School-Ring 2, Germering (DE) 82110

( * ) Notice: Subject to any disclaimer, the term of this patent is extended or adjusted under 35 U.S.C. 154(b) by 124 days.

(21) Appl. No.: 10/070,588

(22) PCT Filed: Sep. 8, 2000

(86) PCT No.: PCT/EP00/08827

§ 371 (c)(1),
(2), (4) Date: Oct. 15, 2002

(87) PCT Pub. No.: WO01/20026

PCT Pub. Date: Mar. 22, 2001

(30) Foreign Application Priority Data

Sep. 10, 1999 (EP) .................. 99118120

(51) Int. Cl.
- C07H 21/04 (2006.01)
- C12Q 1/68 (2006.01)
- C12N 15/00 (2006.01)
- C12P 21/06 (2006.01)

(52) U.S. Cl. ................. 536/23.5; 536/22.1; 435/320.1; 435/69.1; 435/6; 435/325

(58) Field of Classification Search ................ 530/350; 425/69.1, 6, 7.1, 325
See application file for complete search history.

(56) References Cited

U.S. PATENT DOCUMENTS 6,821,724 B1 * 11/2004 Mittman et al. ................ 435/6

FOREIGN PATENT DOCUMENTS

| EP | 1 024 193 | 8/2000 |
| WO | WO 99/48915 | 9/1999 |

OTHER PUBLICATIONS

Whang et al., Genomics 30: 293298, 1995.*
Bertilsson, G. et al., "Identification Of A Human Nuclear Receptor Defines A New Signaling Pathway For CYP3A Induction," *Proc. Natl. Acad. Sci. USA*, 95:12208-12213 (1998).

Dotzlaw, H. et al., "The Human Organ Receptor PXR Messenger RNA is Expressed In Both Normal And Neoplastic Breast Tissue," *Clinical Cancer Research* 5:2103-2107 (1999).
Jones, S. et al., "The Pregnane X Receptor: A Promiscuous Xenobiotic Receptor That Has Diverged During Evolution," *Molecular Endocrinology*, 14:27-39 (2000).
Kliewer, S. et al., "An Orphan Nuclear Receptor Activated By Pregnanes Defines A Novel Steroid Signaling Pathway," *Cell* 92:73-82 (1998).
Lehmann, J. et al., "The Human Orphan Receptor PXR Is Activated By Compounds That Regulate CYP3A4 Gene Expression And Cause Drug Interactions," *Journal of Clinical Investigation* 102:1016-1023 (1998).
Pascussi, J.-M. et al., "Evidence for the Presence of a Functional Pregnane X Receptor Response Element in the CYP3A7 Promoter Gene," *Biochemical and Biophysical Research Communications*, 260:377-381 (1999).
Zhang, H. et al., "Rat Pregnane X Receptor: Molecular Cloning, Tissue Distribution, And Xenobiotic Regulation," *Archives of Biochemistry and Biophysics* 368:14-22 (1999).

* cited by examiner

Primary Examiner—Eileen B. O'Hara
Assistant Examiner—Gyan Chandra
(74) Attorney, Agent, or Firm—Ropes & Gray; Jane T. Gunnison; Katherine A. Helm

(57) ABSTRACT

Described are general means and methods of diagnosing and treating the phenotypic spectrum as well as the overlapping clinical characteristics with several forms of inherited abnormal expression and/or function of the hPXR gene. In particular, polynucleotides of molecular variant hPXR gene which, for example, are associated with insufficient metabolization and/or sensitivity of drugs, and vectors comprising such polynucleotides are provided. Furthermore, host cells comprising such polynucleotides or vectors and their use for the production of variant hPXR proteins are described. In addition, variant hPXR proteins and antibodies specifically recognizing such proteins as well as transgenic non-human animals comprising the above-described polynucleotide or vectors are provided. Described are also methods for identifying and obtaining inhibitors for therapy of disorders related to the malfunction of the hPXR gene as well as methods of diagnosing the status of such disorders. Pharmaceutical and diagnostic compositions comprising the above-described polynucleotides, vectors, proteins, antibodies and inhibitors by the above-described method are provided. Said compositions are particularly useful for diagnosing and treating various diseases with drugs that are substrates, inhibitors or modulators of the hPXR gene product.

9 Claims, 7 Drawing Sheets

Exon1a & Exon1b
<u>TCAAGTGCTGGACTTGGGAC</u>TTAGGAGGGGCAATGGAGCCGCTTAGTGCCTACATCTGACTTGGACTGAAA
TATAGGTGAGAGACAAGATTGTCTCATATCCGGGGAAATCATAACCTATGACTAG<u>GACGGGAAGAGG
AAGCACTGCCTTTACTTCAGTGGGAATCTCG→AGCCTCAGCCTGCAAGCCAAGTGTTCACAGTGAAA
AAAGCAAGAGAATAAGCTAATACTCCTGTCCTGAAC→AAAGGCAGCGGCTCCTTGGTAAAGCTACTC
CTTGATCGATCCTTTGCACCGGATTGTTCAAAGTGGACCCCAGGG→TGAGAAGTCGGAGCAAAGAAC
TTACCACCAAGCAGG</u>TATGGTTTTTCTTTCTTTCTCTTTTGCTGGGGGCTGACCGCCCTTCAGCTCCAGCCA
AAAGATGTGTGTGAACACAAATATACCTTCTGTTT<u>GAGGTCAGCATCATAGTGGG</u>TCGTGAATCATGTTGGC
CTTGCTGCTGTCTCCTCATTTCTAGGGTGAAAAAAAAAAAGCATGAAAACAATCACTTAATGTTGAGCCCC
ATTACTGATGCTCTCTGGTCCTGCACTAGCCTCCTAGAAAAATCACCACAGCCTTAACTACTGCATGAGTTA
CCACAAGTCA<u>CACATACAACCAGCTCCCT</u>GTTACAGGGCTGGAGTCCCTGGACCCAGGAAATACCACCTCC
AAGGACTG<u>T→G</u>GGGAGCTGGGGACTATGGGAACTGGGATCAACTCAGTCCTGATTCCTTTTGGCCTGCTG
GGTTAGTGCTGGCAGCCCCC<u>C→/T</u>GAGGCCAAGGACAGCAGC<u>ATG</u>ACAGTCACCAGGACTCACCACT
TCAAGGAGGGGTCCCTCAGAGCACCTGCCATACCCCTGCACAGTGCTGCGGCTGAGTTGGCTTCAAA
CCA<u>GT</u>GAGTTTTCTACCTCTACTATTGAAAGGGCACCTTGTCCCACAGAACC<u>GAGTCTTGCCTGCATGTGG</u>

Exon2
<u>CTGAGGCCTCTACACAT</u>CCCTGTCCAGTCTTTTCATTCTC<u>T→C</u>GTGGTTTTCTCATTTCT<u>AG</u>TCCAAGAGGC
CCAGAAGCAAAC<u>CT</u>GGAGGTGAGACCCAAAGAAAGCTGGAACCATGCTGACTTTGTACACTGT<u>G→A</u>
AGGACACAGAGTCTGTTCCTGGAAAG<u>C→T</u>CCAGTGTCAACGCAGATGAGGAAGTC<u>G→</u>AGAGGTCCC
CAAATCTGCCGTGTATGTGGGGACAAGGCCACTGGCTATCACTTCAATGTCATGACATGTGAAGGAT
GCAAGGGCTTTTTCAG<u>GT</u>AGAGTTACCCATCAGCCTTCACCCACGTGCCACCACTGACCCACT<u>GGGTAAC
ATCTCAGGGCCT</u>

Exon3
<u>CTGGGACGCAAAGGCTAGT</u>GTCCCCCTCCCCGAGTCGGTAGGGGCTGGGGAGGGAGGTGGTATGGCCCGG
AGCCCCAGGCCGAGGGCCCGGGCACCCGTGCAT<u>C→T</u>CCCCCTTCTGCTCCCCATTCTCTCAC<u>AG</u>GAGGGC
CATGAAACGCAACGCCCGGCT<u>G→C</u>AGGTGCCCCTTCCGGAAGGGCGCCTGCGAGATCACCCGGAAG
ACCCGGCCGACAGTGCCAGGCCTGCCGCCTGCGCAAGTGCCTGGAGAG<u>C→T</u>GGCATGAAGAAGGAGA
<u>GT</u>GAGCAGTGGGCGCGCGGGCGGGCCGGCGCCGGGGTGCACGGCTCTGAGTAAGGACGTGCCGTGGGTGT
GT<u>→G</u>GCATGCTTGTGTGGAGATGCGCGCCGAGTGTGCGCGTGAACACACGTGCACATGTGAGCTGG<u>TGTCC
GTGTGCAACAGG</u>

Exon4
<u>TAACGGCTTCTGCTGCCTT</u>GAGAGGGTTACACAGTGGCTCTCCAGGGGGCTGGAGGCTCACCAGGGGCACG
TGTGCCTGAGCCAGCCTCACTGTCCCTGC<u>AG</u>TGATCATGTCCGACGAGGCCGTGGAGGAGAGGCGGGC
CTTGATCAAGCGGAAGAAAAGTGAACGGACAGGGACTCAGCCACTGGGA<u>G→</u>ATGCAGGGGCTGACA
GAGGAGCAGCGGATGATGATCAGGGAGCTGATGGACGCTCAGATGAAAACCTTTG<u>A→</u>GCAC<u>T→</u>CAC
CTTCTCCCATTTCAAGAATTTCCGG<u>GT</u>AGGAGGAACTGCACAGTGACCCGAGGTGTCACTGCCATCTTCA
TTCTCACATAGAAACTGAGGTTCCCCAAGGATAAGAAACTTATACAAGGTCACAGCTAATCAGTGGTGG<u>AG
GGTAGATTTGGAGAGCT</u>

Exon5
<u>CTGAGTTGGGACCTGTCT</u>ATGAAAGCACATGCTGTCTCTCCTCTGTCCACCTCCTGGCATGTGTCCT<u>AG</u>CTG
CCAGGGGTGCTTAGCAGTGG<u>C→</u>TTGCGAGTTGCCAGAGTCTCTGCAGGCCCCATCGAGGGAAGAAG
CTGCCAAGTGGAGCCAGGTCCGGAAAGATCTGTGCTCTTTGAAGGTCTCTCTGCAGCTGCGGGGGA
GGATGGCAGTGTCTGGAACTACAAACCCCCAGCCGACAGTGG<u>C→</u>TGGGAAAGAGATCTTCTCCCTG
CTGCCCCACATGGCTGACATGTCAACCTACATGTTCAAAGGCATCATCAGCTTTGCCAAAGTCATCTC
CTACTTCAG<u>GT</u>AGGACATGGAGACTGGGTGGTTGGGTGTGGAAAAGAACTGGAAGTGGCCAG<u>GAGGTTCA
AAGGGCCTGG</u>

Fig 4

Exons 6&7
CTGCTGGTGCCGGCCTGTGGGCTGCCTCCCAGGGAGCTGTCCTCCCCTCCCCATCCTTGCTGCCAGGGACTT
GCCCATCGAGGACCAGATCTCCCTGCTGAAGGGG→AGCCGCTTTCGAGCTGTGTCAACTGAGATTCA
ACACAGTGTTCAACGCGGAGACTGGAACCTGGGAGTGTGGCCGGCTGTCCTACTGCTTGGAAGACAC
TGCAGGTGCCCGAGAGAGCCTGCCTGCCCTGGCAGAGGGAGGGAAACACTGCAGTTATGGGAGGAAGGGA
GCTACGCCAGGATATGCAGGTTCTGGGATGGCAG→AGGCAGGAAGATGGAATGGTGGAAAACAAGA→GT
ATTGGTGAGGGATGATTAGATCTTGGTCAGCTTGCTGAGAAGCTGCCCCTCCATC→TCTGTTACCATCCAC
AGGTGGCTTCCAGCAACTTCTACTGGAGCCCATGCTGAAATTCCACTAC→TATGCTGAAGAAGCTGC
AGCTGCATGAGGAGGAGTATGTGCTGATGCAGGCCATCTCCCTCTTCTCCCCAGGTGAGGATCTCCCC
TAGGCTGCCTGACATCCCCCCC→TAGCCTTATCTGCCCTCCCCAGGGAAGGTCCCAGTC

Exon 8
GAGCAATGCCCTGACTCTGGGCTGGACTGAGCTTGTCTTTGCCCCATGATCTTGCACCACACCTCCCTCCCC
TCCAGACCGCCCAGGTGTGCTGCAGCACCGCGTGGTGGACCAGCTGCAGGAGCAATTCG→ACCATTA
CTCTGAAGTCCTACATTGAATGCAATCGGCCCCAGCCTGCTCATAGGTGAGCACAGCAGGGGGTGAGG
ACCCGTGAGGGTGATGTGAGG→AGAGCCGAGGTTCAGGGAAATTGCCCAAGACTTCATGGCCAGAGGG

Exon 9
TGCTTGTGCAGCCTCAGAGCAGCCCTGAGGCTTGTGGGTCAGGGCGGGCTGCACCCACAATCTTTTCTCTGG
CTGGCATGCAGGTTCTTGTTCCTGAAGATCATGGCTATGCTCACCGAGCTCCGCAGCATCAATGCTCA
GCACACCCAGCGGCTGCTGCGCATCCAGGACATACACCCCTTTGCTACGCCCTCATGCAGGAGTTG
TTCGGCATCACAGGTAGCTGAGCG→AGCTGCCCTTGGG→ATGACACCTCCGAGAGGCAGCCAGACC
CAGAGCCCTCTGAGCCGCCACTCCCGGGCCAAGACAGATGGACACTGCCAAGAGC

Fig 4 cont.

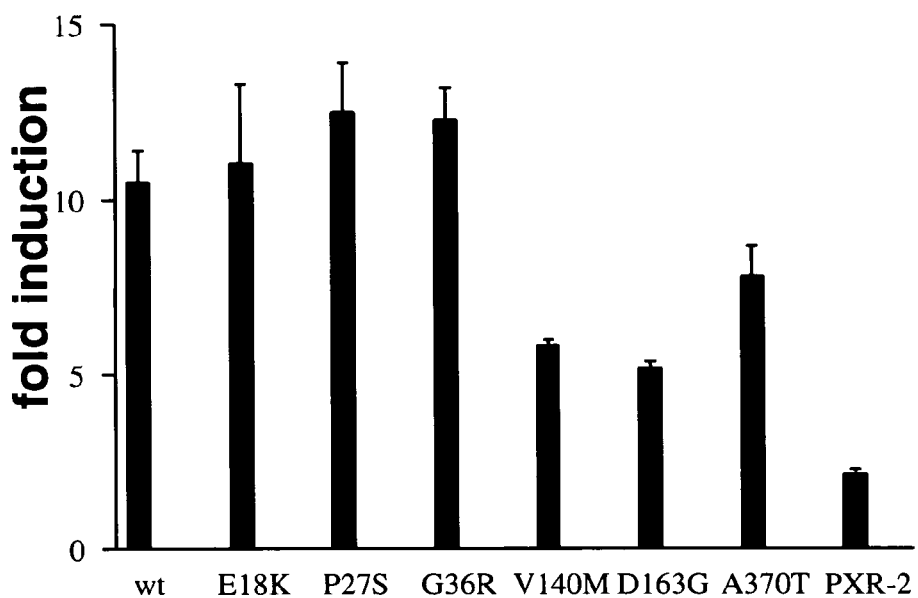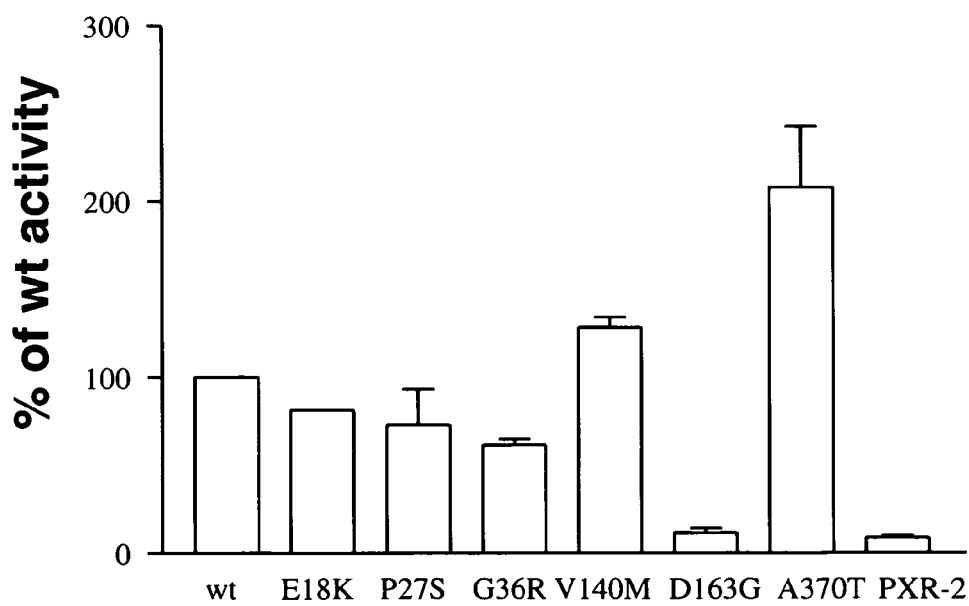
Fig 6

POLYMORPHISMS IN THE HUMAN HPXR GENE AND THEIR USE DIAGNOSTIC AND THERAPEUTIC APPLICATIONS

FIELD OF THE INVENTION

The present invention relates generally to means and methods of diagnosing and treating the phenotypic spectrum as well as the overlapping clinical characteristics with several forms of inherited abnormal expression and/or function of the human pregnane X receptor (hPXR) gene. In particular, the present invention relates to polynucleotides of molecular variant hPXR gene which, for example, are associated with abnormal drug response or individual predisposition to several common cancers caused by environmental carcinogens, and to vectors comprising such polynucleotides. Furthermore, the present invention relates to host cells comprising such polynucleotides or vectors and their use for the production of variant hPXR proteins. In addition, the present invention relates to variant hPXR proteins and antibodies specifically recognizing such proteins. The present invention also concerns transgenic non-human animals comprising the above-described polynucleotide or vectors. Moreover, the present invention relates to methods for identifying and obtaining drug candidates and inhibitors for therapy of disorders related to the malfunction of the hPXR gene as well as to methods of diagnosing the status of such disorders. The present invention furthermore provides pharmaceutical and diagnostic compositions comprising the above-described polynucleotides, vectors, proteins, antibodies, and drugs and inhibitors obtainable by the above-described method. Said compositions are particularly useful for diagnosing and treating various diseases with drugs that are substrates, inhibitors or modulators of the hPXR gene or their product.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

Members of the cytochrome P-450 (CYP) family of hemoproteins metabolise a wide variety of endogenous substrates such as steroid hormones, and of xenobiotics including carcinogens, toxins and drugs(1,2). Of the human CYP proteins, those of the CYP3A subfamily are of a major importance, since collectively, they are by far the most abundant of all the human CYP isoforms. Moreover, their substrate specificity is extremely broad; accordingly, many structurally diverse compounds are, exclusively or to some extent, substrates for CYP3A proteins. Based on the data available it is generally assumed that all CYP3A isoforms have similar substrate spectra; however, limited studies indicate the possibility of differences (3). All CYP3A isoforms are localized in organs of particular importance to drug disposition (gastrointestinal tract, kidney and liver).

At least three functional CYP3A proteins exist in humans. The CYP3A4 monooxygenase is the predominant cytochrome P450 in human liver and small bowel. The protein displays a broad substrate specificity and it metabolises more than 60% of all drugs that are currently in use, including contraceptive steroids, antidepressants, benzodiazepines, immunosuppressive agents, imidazole antimicotics, and macrolide antibiotics (4,5). In addition, CYP3A4 plays a major role in the protection from environmental toxins. For example, the protein metabolizes aflatoxin B1, which has been implicated in the etiology of liver cancer, which is a major cause of premature death in many areas of Africa and Asia. Aflatoxin B1 is a mycotoxin produced by species of *Aspergillus*, and human exposure results principally from the ingestion of stored foodstuffs contaminated with the mold. Carcinogenicity is associated with its conversion to 8,9-oxide by the hepatic cytochrome P450-dependent monooxygenase system. Forrester et al. (6) found that the rates of metabolic activation of aflatoxin B1 were highly correlated with the level of proteins of the CYP3A gene family in the microsomes. Furthermore, Paolini et al. (7) found significant increases in CYP3A in the lungs of rats treated with high doses of beta-carotene. Consequently, it was proposed that correspondingly high levels of CYP3A4 in humans would predispose an individual to cancer risk from the bioactivated tobacco-smoke procarcinogens, thus explaining the cocarcinogenic effect of beta-carotene in smokers. All this implies that individual variation in the CYP3A4 activity could influence the efficacy of a variety of drug therapies as well as the individual predisposition to several major cancers caused by environmental carcinogens.

A considerable variation in the CYP3A4 content and catalytic activity has been, indeed, described in the general population. For example, the metabolic clearance of the gene substrates exhibits a unimodal distribution with up to 20-fold interindividual variability. The activities of the CYP3A4 protein in liver biopsies vary up to 30-fold (8). Furthermore, many common drugs alter the expression levels of the gene (induction or repression) and the extent of this phenomenon is individually variable. The inducers of CYP3A4 expression include commonly used drugs such as the glucocorticoid dexamethasone, the antibiotic rifampicin, and the antimycotic clotrimazole. The inducibility of CYP3A4 expression, combined with the diverse range of substrates, creates a potential for potentially harmful drug interactions involving this isozyme in patients undergoing therapies with multiple drugs.

CYP3A3 is a very closely related isoform to CYP3A4 (>more than 98% cDNA sequence similarity), but it is not known whether this reflects a separate gene product or an allelic variant. By contrast, CYP3A5 is a gene distinct from CYP3A4 and it is expressed polymorphically both in the adult and fetal liver and in the kidney and intestine. In adult Caucasians, the mRNA and the protein were detected in the liver of 10 to 30% of samples, while the protein was detected in the kidney and intestine of 70% of subjects (Ref. (9) and references therein). A point mutation described in the CYP3A5 gene which possibly results in the synthesis of an unstable protein, may account for the polymorphic expression of this enzyme (9). CYP3A7 is the third functional CYP3A isoform. CYP3A7 was originally isolated from a fetal liver but it was subsequently found in 54% of adult livers (10).

Tests to estimate the inducibility and the activity of CYP3A isozymes in an individual patient would be of obvious relevance for the optimization of therapies with drugs which are their substrates, and for the prevention of the associated side effects. Direct estimates of the activities of CYP3A isozymes in liver biopsies are possible but impracticable for both ethical and cost reasons. The indirect in vivo tests of CYP3A4 activity such as the erythromycin breath test or the 6-β-hydroxycortisol test pose ethical problems such as the invasive administration of undesirable probe substances and they are obviously unsuited for routine testing. In addition, the lack of correlation between these tests questions their informative value regarding the CYP3A4 activity (11).

A major portion (83%) of the interindividual CYP3A4 variability has been attributed to genetic factors (12). The establishment of a genetic test for the activity of CYP3A4 and of the other CYP3A isozymes should be possible, assuming the prior identification of those factors. Genetic variance affecting the activity and the expression of CYP3A isozymes could be localized in the genes itself, or in one or more of their regulators. A comparison of the three originally published sequences of the best characterized CYP3A gene, CYP3A4, suggested the existence of polymorphisms affecting the amino acid sequence of the CYP3A4 protein (13). Unfortunately, this observation has not been, to our knowledge, confirmed in the general population. More recently, a polymorphism (CYP3A4-W) has been described in the nifedipine-specific response element of the CYP3A4 promoter (14). Its presence associates with a more advanced prostate tumor stage (14). Felix et al. (15) examined this polymorphism in 99 de novo and 30 treatment-related leukemias. In all treatment-related cases, there was prior exposure to one or more anticancer drugs metabolized by CYP3A, such as epipodophyllotoxins. These data suggest that individuals with the CYP3A4-W polymorphism may be at increased risk for treatment-related leukemia and that epipodophyllotoxin metabolism by CYP3A4 may contribute to the secondary cancer risk. At present it is unclear if the polymorphism influences the expressivity or inducibility of the CYP3A4 protein. A first published analysis suggests that it has no effect on the basal expression level of CYP3A4 (8). A point mutation was described in the CYP3A5 (9), whereas no mutations have been reported in CYP3A7.

Experiments with amino acid exchanges artificially introduced into the CYP3A4 gene indicate that the function of the family members may be quite sensitive to amino acid exchanges (16–21). Besides amino acid exchanges, silent polymorphisms and those localized in untranslated or intronic sequences also could influence the expression level of these genes. Alternatively, such polymorphisms could serve as markers for nearby, unidentified polymorphisms. This effect is known as linkage, i.e. defined polymorphisms serve as markers for phenotypes that they are not causative for.

A major breakthrough in the understanding of the CYP3A expression and inducibility took place in 1998 when three research groups independently showed that the expression of CYP3A4 is regulated by a member of the orphan nuclear receptor family termed hPXR (pregnane X receptor), or PAR (22–24). Upon treatment with inducers of CYP3A4, hPXR binds to the rifampicin/dexamethasone response element in the CYP3A4 promoter as a heterodimer with the 9-cis retinoic acid receptor (RXR). Northern blot analysis detected most abundant expression of hPXR in liver, colon, and small intestine, i.e. in the major organs expressing CYP3A4. The available evidence suggests that human hPXR serves as a key transcriptional regulator of the CYP3A4 gene. A recent report describes the induction of CYP3A7 mediated by hPXR suggesting that all members of the family may be regulated by this common transcriptional activator (25).

It is clear that naturally occurring mutations in hPXR, if they exist can have effects on drug metabolization and efficacy of therapies with drugs, in particular in cancer treatment. It is unknown, however, how many of such variations exist, and with what frequency and at what positions in the human hPXR gene.

Accordingly, means and methods for diagnosing and treating a variety of forms of individual drug intolerability and inefficacy of drug therapy which result from hPXR gene polymorphisms that interfere e.g., with chemotherapeutic treatment of diseases, in particular cancer, was hitherto not available but are nevertheless highly desirable.

Thus, the technical problem of the present invention is to comply with the needs described above.

The solution to this technical problem is achieved by providing the embodiments characterized in the claims.

SUMMARY OF THE INVENTION

The present invention is based on the finding of novel, so far unknown variations in the nucleotide sequences of the hPXR gene and the population distribution of these alleles. Based upon the knowledge of these novel sequences diagnostic tests and reagents for such tests were designed for the specific detection and genotyping of hPXR alleles in humans, including homozygous as well as heterozygous, frequent as well as rare alleles of the hPXR gene. The determination of the hPXR gene allele status of humans with such tests is useful for the optimization of therapies with the numerous substrates of CYP3A4 and CYP3A7. It may also be useful in the determination of the individual predisposition to several common cancers caused by environmental carcinogens.

In a first embodiment, the invention provides polynucleotides of molecular variant hPXR genes and embodiments related thereto such as vectors, host cells, variant hPXR proteins and methods for producing the same.

In yet another embodiment, the invention provides methods for identifying and obtaining drug candidates and inhibitors of hPXR for therapy of disorders related to acquired drug hypo- or hypersensitivity as well as methods of diagnosing the status of such disorders.

In a further embodiment, the invention provides pharmaceutical and diagnostic compositions comprising the above-described polynucleotides, vectors containing the same, proteins, antibodies thereto, and drugs and inhibitors obtainable by the above-described method.

The pharmaceutical and diagnostic compositions, methods and uses of the invention are useful for the diagnosis and treatment of cancer and other diseases the therapy of which is dependent on drug treatment and tolerance. The hovel variant forms of hPXR gene according to the invention provide the potential for the development of a pharmacodynamic profile of drugs for a given patient.

DESCRIPTION OF THE INVENTION

The finding and characterization of variations in the hPXR genes, and diagnostic tests for the discrimination of different hPXR alleles in human individuals provide a very potent tool for improving the therapy of diseases with drugs that are targets of the CYP3A4 or CYP3A7 gene product, and whose metabolization is therefore dependent on CYP3A4 or CYP3A7. The diagnosis of the individual allelic hPXR status permits a more focused therapy, e.g., by opening the possibility to apply individual dose regimens of drugs. It may also be useful as prognostic tool for therapy outcome. Furthermore, diagnostic tests to genotype hPXR, and novel hPXR variants, will not only improve therapy with established drugs and help to correlate genotypes with drug activity or side effects. These tests and sequences also provide reagents for the development of novel inhibitors that specifically modulate the activity of the individual types of hPXR.

Thus, the present invention provides a novel way to exploit molecular biology and pharmacological research for drug therapy while bypassing their potential detrimental effects which are due to expression of variant hPXR genes.

Accordingly, the invention relates to a polynucleotide selected from the group consisting of:

(a) a polynucleotide having the nucleic acid sequence of SEQ ID NO: 56, 57, 60, 61, 64, 65, 68, 69, 72, 73, 76, 77, 80, 81, 84, 85, 88, 89, 92, 93, 96, 97, 100, 101, 104, 105, 108, 109, 112, 113, 116, 117, 120, 121, 124, 125, 128, 129, 132, 133, 136, 137, 140, 141, 144, 145, 148, 149, 152, 153, 156, 157, 160, 161, 164, 165, 166, 168, 170, 172, 174 or 176;

(b) a polynucleotide encoding a polypeptide having the amino acid sequence of SEQ ID NO: 167, 169, 171, 173, 175 or 177;

(c) a polynucleotide encoding a hPXR polypeptide, wherein said polynucleotide is having at a position corresponding to position −201, −131, −57, −42, 52, 79, 106, 225, 315, 418, 488, 492, 543, 696, 834, 984, 1108, 1308 or 1320 of the hPXR gene (Accession No: gi3769538, wherein the C of the CTG translation initiation site at position 280 has been numbered +1), at position corresponding to position −100 or −20 of the hPXR gene (Accession No: gi3769536, wherein the A of the start codon ATG at position 60 has been numbered +1), at a position corresponding to position −29 of Intron 2 of the hPXR gene (Accession No: gi3769538, wherein Exon 3 starts at position 477), at a position corresponding to position +72 of Intron 3 of the hPXR gene (Accession No: gi3769538, wherein Exon 3 ends at position 610), at a position corresponding to position +99 of Intron 6 of the hPXR gene (Accession No: gi3769538, wherein Exon 6 ends at position 1216), at a position corresponding to position −73 or −17 of Intron 6 of the hPXR gene (Accession No: gi3769538, wherein Exon 7 starts at position 1217), at a position corresponding to position +36 of Intron 7 of the hPXR gene (Accession No: gi3769538, wherein Exon 7 ends at position 1333) or at a position corresponding to position +43 of Intron 8 of the hPXR gene (Accession No: gi3769538, wherein Exon 8 ends at position 1439) a nucleotide exchange, a nucleotide deletion, an additional nucleotide or a nucleotide deletion and a nucleotide exchange;

(d) a polynucleotide encoding a hPXR polypeptide, wherein said polynucleotide is having at a position corresponding to position −201, −131, 52, 106, 418, 834, 1108, 1308 or 1320 of the hPXR gene (Accession No: gi3769538, wherein the C of the CTG translation initiation site at position 280 has been numbered +1) or at a position corresponding to position +99 of Intron 6 of the hPXR gene (Accession number: gi3769538, wherein Exon 6 ends at position 1216) or at a position corresponding to position +43 of the Intron 8 of the hPXR gene (Accession number: gi3769538, wherein Exon 8 ends at position 1439) an A, at a position corresponding to position −57, 79, 315, 543, 696 or 984 of the hPXR gene (Accession No: gi3769538, wherein the C of the CTG translation initiation site at position 280 has been numbered +1) or at a position corresponding to position −29 of Intron 2 of the hPXR gene (Accession No: gi3769538, wherein Exon 3 starts at position 477), at a position corresponding to position −17 of Intron 6 of the hPXR gene gene (Accession number: gi3769538, wherein Exon 7 starts at position 1217) or at a position corresponding to position +36 of Intron 7 of the hPXR gene gene (Accession number: gi3769538, wherein Exon 7 ends at position 1333) a T, at a position corresponding to position −20 of the hPXR gene (Accession number No: gi3769536, wherein the A at the start codon ATG at position 60 has been numbered +1) a deletion, at position corresponding to position −42, 225 or 492 of the hPXR gene (Accession No: gi3769538, wherein the C of the CTG translation initiation site at position 280 has been numbered +1) a C or at a position corresponding to position 488 of the hPXR gene (Accession No: gi3769538, wherein the C of the CTG translation initiation site at position 280 has been numbered +1), at a position corresponding to position −100 of the hPXR gene (Accession No: gi3769536, wherein the A of the start codon ATG at position 60 has been numbered +1), at a position corresponding to position +72 of Intron 3 of the hPXR gene (Accession No: gi3769538, wherein Exon 3 ends at position 610) or at a position corresponding to position −73 of Intron 6 of the hPXR gene gene (Accession No: gi3769538, wherein Exon 7 starts at position 1217) a G;

(e) a polynucleotide encoding a hPXR polypeptide, wherein said polypeptide comprises an amino acid substitution at position 18, 27, 36, 140, 163 or 370 of the hPXR polypeptide (Accession No: gi3769538, wherein the C of the start codon CTG is at position 280); and (f) a polynucleotide encoding a hPXR polypeptide, wherein said polypeptide comprises an amino acid substitution of E to K at position 18, of P to S at position 27, of G to R at position 36, of V to M at position 140, of D to G at position 163 or of A to T at position 370 of the hPXR polypeptide (Accession No: gi3769538).

In the context of the present invention the term "molecular variant" hPXR gene or protein as used herein means that said hPXR gene or protein differs from the wild type hPXR gene or protein by way of nucleotide substitution(s), addition(s) and/or deletion(s) (cDNA sequences for the hPXR gene in Bertilsson, Proc Natl Acad Sci USA 95 (1998), 12208–13; Lehmann, J Clin Invest. 102 (1998), 1016–23; Accession numbers: AF061056 (gi3511137), AF084645 (gi376938), AF084644 (gi376936), AJ009936 (gi5852062), AJ009937 (gi5852066). The numbering of the polymorphisms refers to the sequences gi3769536 for the variants corresponding to position −100 or −20 of the hPXR gene (Accession No: gi3769536, wherein the A of the start codon ATG at position 60 has been numbered +1) or gi3769538 for all the other variants of the hPXR gene. Preferably, said nucleotide substitution(s) result(s) in a corresponding change in the amino acid sequence of the hPXR protein.

The term "corresponding" as used herein means that a position is not only determined by the number of the preceding nucleotides and amino acids, respectively. The position of a given nucleotide or amino acid in accordance with the present invention which may be deleted, substituted or comprise one or more additional nucleotide(s) may vary due to deletions or additional nucleotides or amino acids elsewhere in the gene or the polypeptide. Thus, under a "corresponding position" in accordance with the present invention it is to be understood that nucleotides or amino acids may differ in the indicated number but may still have similar neighboring nucleotides or amino acids. Said nucleotides or amino acids which may be exchanged, deleted or comprise additional nucleotides or amino acids are also comprised by the term "corresponding position". Said nucleotides or amino acids may for instance together with their neighbors form sequences which may be involved in the regulation of gene expression, stability of the corresponding RNA or RNA editing, as well as encode functional domains or motifs of the protein of the invention.

The nomenclature of the variants comprising single nucleotide polymorphisms (SNPs) as listed in column two of table 4 is based on Antonarakis and the Nomenclature Working Group (Antonarakis, Hum Mutat 11 (1998), 1–3). As the translation initiation site the CTG with the C at position 280 of the cDNA (gi 3769538) is numbered +1. The nucleotide 5' to +1 is numbered −1. SNPs that are located in introns are indicated by the number of nucleotides upstream (+) or downstream (−) the nucleotide position of the first or last nucleotide of an exon. SNPs which are located in Exon 1b or Intron 1b are indicated by numbers referring to the A(+1) of the start ATG which would be at position 60 of the aforementioned nomenclature having Accession No: gi3769536.

It is furthermore to be understood that one nucleotide adjacent to a position where an exon ends or starts as indicated above, an intron starts or ends. A sequence comprising said exon to intron or intron to exon transition will also be referred to as exon-intron boundary hereinafter. Usually, consecutive numbering is applied for all exons and/or all introns. Preferably, Intron 1 follows Exon 1, Intron 2 follows Exon 2 and so on and so forth. In cases where alternative exons may be used, said alternatively used exons may be designated by letters. Thus, two alternatively used "Exons 1" may referred to as Exon 1a and Exon 1b, respectively. In the case of Exon 1a, Introh 1a follows Exon 1a and Intron 1 b follows Exon 1 b.

In accordance with the present invention, the mode and population distribution of novel so far unidentified genetic variations in the hPXR gene have been analyzed by sequence analysis of relevant regions of the human hPXR gene from many different individuals. It is a well known fact that genomic DNA of individuals, which harbor the individual genetic makeup of all genes, including hPXR can easily be purified from individual blood samples. These individual DNA samples are then used for the analysis of the sequence composition of the hPXR gene alleles that are present in the individual which provided the blood sample. The sequence analysis was carried out by PCR amplification of relevant regions of the hPXR gene, subsequent purification of the PCR products, followed by automated DNA sequencing with established methods (ABI dye terminator cycle sequencing).

One important parameter that had to be considered in the attempt to determine the individual hPXR genotype and identify novel hPXR variants by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel hPXR gene polymorphisms (homozygous and heterozygous) are described in the examples below.

The mutations in the hPXR gene detected in accordance with the present invention are illustrated in Table 4, Table 5 and FIG. 4. The methods of the mutation analysis followed standard protocols and are described in detail in the examples. In general such methods to be used in accordance with the present invention for evaluating the phenotypic spectrum as well as the overlapping clinical characteristics with other forms of drug metabolization and altered tolerance to drugs in patients with mutations in the hPXR gene encompass for example haplotype analysis, single-strand conformation polymorphism analysis (SSCA), PCR and direct sequencing. On the basis of thorough clinical characterization of many patients the phenotypes can then be correlated to these mutations as well as to mutations that had been described earlier.

As is evident to the person skilled in the art this new molecular genetic knowledge can now be used to exactly characterize the genotype of the index patient where a given drug takes an unusual effect and of his family.

Over the past 20 years, genetic heterogeneity has been increasingly recognized as a significant source of variation in drug response. Many scientific communications (Meyer, Ann. Rev. Pharmacol. Toxicol. 37 (1997), 269–296 and West, J. Clin. Pharmacol. 37 (1997), 635–648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, Nature Biotechnology, 15 (1997), 954–957; Marshall, Nature Biotechnology, 15 (1997), 1249–1252).

In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, Clin. Pharmacokinet. 32 (1997), 210–256; Engel, J. Chromatogra. B. Biomed. Appl. 678 (1996), 93–103). For the providers of health care, such as health maintenance organizations in the U.S. and government public health services in many European countries, this pharmacogenomics approach can represent a way of both improving health care and reducing overheads because there is a large cost to unnecessary therapies, ineffective drugs and drugs with side effects.

The mutations in the variant hPXR gene sometime result in amino acid deletion(s), insertion(s) and in particular in substitution(s) either alone or in combination. It is of course also possible to genetically engineer such mutations in wild type genes or other mutant forms. Methods for introducing such modifications in the DNA sequence of hPXR gene are well known to the person skilled in the art; see, e.g., Sambrook, Molecular Cloning A Laboratory Manual, Cold Spring Harbor Laboratory (1989) N.Y.

For the investigation of the nature of the alterations in the amino acid sequence of the hPXR proteins computer programs may be used such as BRASMOL that are obtainable from the Internet. Furthermore, folding simulations and computer redesign of structural motifs can be performed using other appropriate computer programs (Olszewski, Proteins 25 (1996), 286–299; Hoffman, Comput. Appl. Biosci. 11 (1995), 675–679). Computers can be used for the conformational and energetic analysis of detailed protein models (Monge, J. Mol. Biol. 247 (1995), 995–1012; Renouf, Adv. Exp. Med. Biol. 376 (1995), 37–45). These analysis can be used for the identification of the influence of a particular mutation on hPXR protein function.

Usually, said amino acid deletion, addition or substitution in the amino acid sequence of the protein encoded by the polynucleotide of the invention is due to one or more nucleotide substitution, insertion or deletion, or any combinations thereof.

The polynucleotide of the invention may further comprise at least one nucleotide and optionally amino acid deletion, addition and/or substitution other than those specified hereinabove, for example those described in the prior art; e.g., (13). This embodiment of the present invention allows the study of synergistic effects of the mutations in the hPXR gene on the pharmacological profile of drugs in patients who bear such mutant forms of the gene or similar mutant forms that can be mimicked by the above described proteins. It is expected that the analysis of said synergistic effects provides deeper insights into drug tolerant or sensitive phenotypes of certain forms of cancer and other diseases. From said deeper insight the development of diagnostic and pharmaceutical compositions related to cancer will greatly benefit.

Thus, in a preferred embodiment, the present invention relates to polynucleotides of molecular variant hPXR gene, wherein the nucleotide deletion, addition and/or substitution result in altered expression of the variant hPXR gene compared to the corresponding wild type gene.

The polynucleotide of the invention may be, e.g., DNA, cDNA, genomic DNA, RNA or synthetically produced DNA or RNA or a recombinantly produced chimeric nucleic acid molecule comprising any of those polynucleotides either alone or in combination. Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions.

In a further preferred embodiment of the vector of the invention, the polynucleotide of the invention is operatively linked to expression control sequences allowing expression in prokaryotic or eukaryotic cells. Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The present invention furthermore relates to host cells transformed with a polynucleotide or vector of the invention. Said host cell may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712–4716; Joyner, Gene Targeting, A Practical Approach, Oxford University Press.

The host cell can be any prokaryotic or eukaryotic cell, such as a bacterial, insect, fungal, plant, animal or human cell. Preferred fungal cells are, for example, those of the genus Saccharomyces, in particular those of the species S. cerevisiae. The term "prokaryotic" is meant to include all bacteria which can be transformed or transfected with a polynucleotide for the expression of a variant hPXR protein or fragment thereof. Prokaryotic hosts may include gram negative as well as gram positive bacteria such as, for example, E. coli, S. typhimurium, Serratia marcescens and Bacillus subtilis. A polynucleotide coding for a mutant form of hPXR variant proteins can be used to transform or transfect the host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of variant hPXR proteins in, e.g., prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The proteins of the invention can then be isolated from the grown medium, cellular lysates, or cellular membrane fractions. The isolation and purification of the microbially or otherwise expressed polypeptides of the invention may be by any conventional means such as, for example, preparative chromatographic separations and immunological separations such as those involving the use of monoclonal or polyclonal antibodies.

Thus, in a further embodiment the invention relates to a method for the production of variant hPXR proteins and fragments thereof comprising culturing a host cell as defined above under conditions allowing the expression of the protein and recovering the produced protein or fragment from the culture.

In another embodiment the present invention relates to a method for producing cells capable of expressing a variant hPXR gene comprising genetically engineering cells with the polynucleotide or with the vector of the invention. The cells obtainable by the method of the invention can be used, for example, to test drugs according to the methods described in Sambrook, Fritsch, Maniatis (1989). Molecular cloning: a laboratory manual. Cold Spring Harbour Laboratory press, Cold Spring Harbour; Peyronneau, Eur J Biochem 218 (1993), 355–61; Yamazaki, Carcinogenesis 16 (1995), 2167–2170. Furthermore, the cells can be used to study known drugs and unknown derivatives thereof for their ability to complement loss of drug efficacy caused by mutations in the hPXR gene. For these embodiments the host cells preferably lack a wild type allele, preferably both alleles of the hPXR gene and/or have at least one mutated from thereof. Alternatively, strong overexpression of a mutated allele over the normal allele and comparison with a recombinant cell line overexpressing the normal allele at a similar level may be used as a screening and analysis system. The cells obtainable by the above-described method may also be used for the screening methods referred to herein below.

Furthermore, the invention relates to variant hPXR proteins and fragments thereof encoded by a polynucleotide according to the invention or obtainable by the above-described methods or from cells produced by the method described above. In this context it is also understood that the variant hPXR proteins according to the invention may be further modified by conventional methods known in the art. By providing the variant hPXR proteins according to the present invention it is also possible to determine the portions relevant for their biological activity or inhibition of the same.

The present invention furthermore relates to antibodies specifically recognizing a variant hPXR protein according to the invention. Advantageously, the antibody specifically recognizes an epitope containing one or more amino acid substitution(s) as defined above.

Antibodies against the variant hPXR protein of the invention can be prepared by well known methods using a purified protein according to the invention or a (synthetic) fragment derived therefrom as an antigen. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. The antibodies can be monoclonal antibodies, polyclonal antibodies or synthetic antibodies as well as fragments of antibodies, such as Fab, Fv or scFv fragments etc. Furthermore, antibodies or fragments thereof to the aforementioned polypeptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the variant hPXR proteins of the invention as well as for the monitoring of the presence of such variant hPXR proteins, for example, in transgenic organisms, and for the identification of compounds interacting with the proteins according to the invention. For example, surface plasmon resonance as employed in the BIAcore system can be used to increase the efficiency of phage antibodies which bind to an epitope of the protein of the invention (Schier, Human Antibodies Hybridomas 7 (1996), 97–105; Malmborg, J. Immunol. Methods 183 (1995), 7–13).

Furthermore, the present invention relates to nucleic acid molecules which represent or comprise the complementary strand of any of the above described polynucleotides or a part thereof, thus comprising at least one nucleotide difference compared to the corresponding wild type hPXR gene nucleotide sequences specified by the above described nucleotide substitutions, deletions and additions. Such a molecule may either be a deoxyribonucleic acid or a ribonucleic acid. Such molecules comprise, for example, antisense RNA. These molecules may furthermore be linked to sequences which when transcribed code for a ribozyme thereby producing a ribozyme which specifically cleaves transcripts of polynucleotides according to the invention.

Furthermore, the present invention relates to a vector comprising a nucleic acid molecule according to the invention. Examples for such vectors are described above. Preferably, the nucleic acid molecule present in the vector is operatively linked to regulatory elements permitting expression in prokaryotic or eukaryotic host cells; see supra.

The present invention also relates to a method for the production of a transgenic non-human animal, preferably transgenic mouse, comprising introduction of a polynucleotide or vector of the invention into a germ cell, an embryonic cell, stem cell or an egg or a cell derived therefrom. The non-human animal can be used in accordance with the method of the invention described below and may be a non-transgenic healthy animal, or may have a disorder, preferably a disorder caused by at least one mutation in the hPXR gene. Such transgenic animals are well suited for, e.g., pharmacological studies of drugs in connection with variant forms of the above described variant hPXR proteins since these proteins or at least their functional domains are conserved between species in higher eukaryotes, particularly in mammals. Production of transgenic embryos and screening of those can be performed, e.g., as described by A. L. Joyner Ed., Gene Targeting, A Practical Approach (1993), Oxford University Press. The DNA of the embryos can be analyzed using, e.g., Southern blots with an appropriate probe.

The invention also relates to transgenic non-human animals such as transgenic mouse, rats, hamsters, dogs, monkeys, rabbits, pigs, *C. elegans* and fish such as torpedo fish comprising a polynucleotide or vector of the invention or obtained by the method described above, preferably wherein said polynucleotide or vector is stably integrated into the genome of said non-human animal, preferably such that the presence of said polynucleotide or vector leads to the expression of the variant hPXR gene of the invention. It may have one or several copies of the same or different polynucleotides of the variant hPXR gene. This animal has numerous utilities, including as a research model for drug tolerability and therefore, presents a novel and valuable animal in the development of therapies, treatment, etc. for diseases caused by deficiency or failure of drug metabolization in the cell. Accordingly, in this instance, the mammal is preferably a laboratory animal such as a mouse or rat.

Preferably, the transgenic non-human animal of the invention further comprises at least one inactivated wild type allele of the hPXR gene. This embodiment allows for example the study of the interaction of various variant forms of hPXR proteins. It might be also desirable to inactivate hPXR gene expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript of the hPXR gene; see also supra. A suitable inducible system is for example tetracycline-regulated gene expression as described, e.g., by Gossen and Bujard (Proc. Natl. Acad. Sci. 89 USA (1992), 5547–5551) and Gossen et al. (Trends Biotech. 12 (1994), 58–62). Similar, the expression of the variant hPXR gene may be controlled by such regulatory elements.

With the variant hPXR polynucleotides and proteins and vectors of the invention, it is now possible to study in vivo and in vitro the efficiency of drugs in relation to particular mutations in the hPXR gene of a patient and the affected phenotype. Furthermore, the variant hPXR proteins of the invention can be used to determine the pharmacological profile of drugs and for the identification and preparation of further drugs which may be more effective for the treatment of, e.g., cancer, in particular for the amelioration of certain phenotypes caused by the respective mutations such as those described above.

Thus, a particular object of the present invention concerns drug/pro-drug selection and formulation of pharmaceutical compositions for the treatment of diseases which are amenable to chemotherapy taking into account the polymorphism of the variant form of the hPXR gene that cosegregates with the affected phenotype of the patient to be treated. This allows the safe and economic application of drugs which for example were hitherto considered not appropriate for therapy of, e.g., cancer due to either their side effects in some patients and/or their unreliable pharmacological profile with respect to the same or different phenotype(s) of the disease. The means and methods described herein can be used, for example, to improve dosing recommendations and allows the prescriber to anticipate necessary dose adjustments depending on the considered patient group.

In a further embodiment the present invention relates to a method of identifying and obtaining an hPXR inhibitor capable of modulating the activity of a molecular variant of the hPXR gene or its gene product comprising the steps of
(a) contacting the variant hPXR protein or a cell expressing a molecular variant gene comprising a polynucleotide of the invention in the presence of components capable of providing a detectable signal in response to drug metabolization, with a compound to be screened under conditions to permit CYP3A4 or CYP3A7 mediated drug metabolization, and
(b) detecting the presence or absence of a signal or increase of a signal generated from the metabolized drug, wherein the presence or increase of the signal is indicative for a putative inhibitor.

The term "compound" in a method of the invention includes a single substance or a plurality of substances which may or may not be identical.

Said compound(s) may be chemically synthesized or produced via microbial fermentation but can also be comprised in, for example, samples, e.g., cell extracts from, e.g., plants, animals or microorganisms. Furthermore, said compounds may be known in the art but hitherto not known to be useful as an inhibitor, respectively. The plurality of compounds may be, e.g., added to the culture medium or injected into a cell or non-human animal of the invention.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties, for example, by the methods described herein or in the literature (e.g. (13) and Lehmann, J Clin Invest 102 (1998), 1016–23). Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art or by using and modifying the methods as described herein. Furthermore, the person skilled in the art will readily recognize which further compounds and/or enzymes may be used in order to perform the methods of the invention, for example, enzymes, if necessary, that convert a certain compound into the precursor which in turn represents a substrate for the CYP3A4 or CYP3A7 protein. Such adaptation of the method of the invention is well within the skill of the person skilled in the art and can be performed without undue experimentation.

Suitable assays which can be employed in accordance with the present invention are described, for example, in Hashimoto, Eur J Biochem 218 (1993), 585–95 wherein transfection assays with chimeric CYP3A4 genes in HepG2 cells are described. Similarly, the variant hPXR genes can be expressed or co-expressed in HepG2 cells and analyzed for their transcriptional activity and catalytic properties of CYP3A4 or CYP3A7. Such an assay can also be used for studying the catalytic properties of the CYP3A4 and CYP3A7 on its substrates such as steroids (testosterone, progesterone, androstenedione, cortisol, 17β-oestradiol, 17α-ethynyloestradiol), antibiotics (erythromycin), immunosuppressive (cyclosporine A), benzodiazepine (midazolam), benzothiazepine derivatives (diltiazem, triazolam), and nifedipine. In particular, such tests are useful to add in predicting whether a given drug will interact in an individual carrying the respective variant CYP3A4, CYP3A7 and/or hPXR gene. A suitable expression system which can be employed in accordance with above described methods of the present invention is also described in (22). In addition heterologous expression systems such as yeast can be used in order to study the stability, binding properties and catalytic activities of the gene products of the variant hPXR gene compared to the corresponding wild type gene product. As mentioned before, the molecular variant hPXR gene and their gene products, particularly when employed in the above described methods, can be used for pharmacological and toxicological studies of the metabolism of drugs. Preferred drugs to be tested in accordance with the methods of the present invention comprise those described above and include, but are not limited to nifedipine, erythromycin, troleandomycin, quinidine, cyclosporin A, 17 α-ethynylestradiol, lidocaine, diltiazem, dexamethasone, RU486, see also supra. Compounds which can be used in accordance with the present invention include peptides, proteins, nucleic acids, antibodies, small organic compounds, ligands, peptidomimetics, PNAs and the like. Said compounds can also be functional derivatives or analogues of known drugs such as from those described above. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art or as described. Furthermore, peptide mimetics and/or computer aided design of appropriate drug derivatives and analogues can be used, for example, according to the methods described below. Such analogs comprise molecules having as the basis structure of known CYP3A4 and CYP3A7-substrates and/or inhibitors and/or modulators; see infra.

Appropriate computer programs can be used for the identification of interactive sites of a putative inhibitor and the hPXR protein of the invention by computer assistant searches for complementary structural motifs (Fassina, Immunomethods 5 (1994), 114–120). Further appropriate computer systems for the computer aided design of protein and peptides are described in the prior art, for example, in Berry, Biochem. Soc. Trans. 22 (1994), 1033–1036; Wodak, Ann. N.Y. Acad. Sci. 501 (1987), 1–13; Pabo, Biochemistry 25 (1986), 5987–5991. The results obtained from the above-described computer analysis can be used in combination with the method of the invention for, e.g., optimizing known inhibitors. Appropriate peptidomimetics and other inhibitors can also be identified by the synthesis of peptidomimetic combinatorial libraries through successive chemical modification and testing the resulting libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220–234 and Dorner, Bioorg. Med. Chem. 4 (1996), 709–715. Furthermore, the three-dimensional and/or crystallographic structure of inhibitors and the hPXR protein of the invention can be used for the design of peptidomimetic drugs (Rose, Biochemistry 35 (1996), 12933–12944; Rutenberg, Bioorg. Med. Chem. 4 (1996), 1545–1558).

In summary, the present invention provides methods for identifying and obtaining compounds which can be used in specific doses for the treatment of specific forms of diseases, e.g., cancer the chemotherapy of which is complicated by malfunctions of the hPXR gene often resulting in an altered activity or level of drug metabolization or sensitive phenotype.

In a preferred embodiment of the method of the invention said cell is a cell, obtained by the method of the invention or is comprised in the above-described transgenic non-human animal.

In a further embodiment the present invention relates to a method of identifying and obtaining an hPXR inhibitor capable of modulating the activity of a molecular variant of the hPXR gene or its gene product comprising the steps of
(a) contacting the variant hPXR protein of the invention with a first molecule known to be bound by hPXR protein to form a first complex of said protein and said first molecule;
(b) contacting said first complex with a compound to be screened; and
(c) measuring whether said compound displaces said first molecule from said first complex.

Advantageously, in said method said measuring step comprises measuring the formation of a second complex of said protein and said inhibitor candidate. Preferably, said measuring step comprises measuring the amount of said first molecule that is not bound to said protein.

In a particularly preferred embodiment of the above-described method of said first molecule is nifedipine, rifampicine or corticosterone. Furthermore, it is preferred that in the method of the invention said first molecule is labeled, e.g., with a radioactive or fluorescent label.

In a still further embodiment the present invention relates to a method of diagnosing a disorder related to the presence of a molecular variant hPXR gene or susceptibility to such a disorder comprising
(a) determining the presence of a polynucleotide of the invention in a sample from a subject; and/or
(b) determining the presence of a variant form of hPXR protein, for example, with the antibody of the invention.

In accordance with this embodiment of the present invention, the method of testing the status of a disorder or susceptibility to such a disorder can be effected by using a polynucleotide or a nucleic acid molecule of the invention, e.g., in the form of a Southern or Northern blot or in situ analysis. Said nucleic acid sequence may hybridize to a coding region of either of the genes or to a non-coding region, e.g. intron. In the case that a complementary sequence is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above-mentioned hPXR gene or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of variant hPXR gene can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985. Furthermore, the mRNA, cRNA, cDNA or genomic DNA obtained from the subject may be sequenced to identify mutations which may be characteristic fingerprints of mutations in the hPXR gene. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above.

Further modifications of the above-mentioned embodiment of the invention can be easily devised by the person skilled in the art, without any undue experimentation from this disclosure; see, e.g., the examples. An additional embodiment of the present invention relates to a method wherein said determination is effected by employing an antibody of the invention or fragment thereof. The antibody used in the method of the invention may be labeled with detectable tags such as a histidine flags or a biotin molecule.

In a preferred embodiment of the present invention, the above described methods comprise PCR, ligase chain reaction, restriction digestion, direct sequencing, nucleic acid amplification techniques, hybridization techniques or immunoassays (Sambrook et al., loc. cit. CSH cloning, Harlow and Lane loc. cit. CSH antibodies).

In a preferred embodiment of the method of the present invention said disorder is cancer.

In a further embodiment of the above-described method, a further step comprising administering to the subject a medicament to abolish or alleviate said variations in the hPXR gene in accordance with all applications of the method of the invention allows treatment of a given disease before the onset of clinical symptoms due to the phenotype response caused by the hPXR gene.

In a preferred embodiment of the method of the invention said medicament are chemotherapeutic agents such as substrates of CYP3A4: paclitaxel (Eur J Drug Metab Pharmacokinet 23 (1998), 417–24), tamoxifen and toremifene (Drug Metab Dispos 27(1999), 681–8; Clin Pharmacol Ther 64 (1998), 648–54; Clin Pharmacol Ther 57 (1995), 628–35), trofosfamide (Cancer Chemother Pharmacol 44(1999), 327–334), cyclophosphamide and ifosfamide (Drug Metab Dispos 27 (1999), 655–66; Cancer Res 58 (1998), 4391–401; Br J Clin Pharmacol 40 (1995), 523–30), taxotere (Pharmacogenetics 8 (1998), 391–401; Clarke, Clin Pharmacokinet 36 (1999), 99–114).

In another preferred embodiment of the above-described methods, said method further comprises introducing (i) a functional and expressible wild type hPXR gene or (ii) a nucleotide acid molecule or vector of the invention into cells.

In this context and as used throughout this specification, "functional" hPXR gene means a gene wherein the encoded protein having part or all of the primary structural conformation of the wild type hPXR protein, i.e. possessing the biological property of metabolizing drugs and controlling the CYP3A4, CYP3A7 gene, respectively. This embodiment of the present invention is suited for therapy of cancer in particular in humans. Detection of the expression of a variant hPXR gene would allow the conclusion that said expression is interrelated to the generation or maintenance of a corresponding phenotype of the disease. Accordingly, a step would be applied to reduce the expression level to low levels or abolish the same. This can be done, for example, by at least partial elimination of the expression of the mutant gene by biological means, for example, by the use of ribozymes, antisense nucleic acid molecules, intracellular antibodies or the above described inhibitors against the variant forms of these hPXR proteins. Furthermore, pharmaceutical products may be developed that reduce the expression levels of the corresponding mutant proteins and genes.

In a further embodiment the invention relates to a method for the production of a pharmaceutical composition comprising the steps of any one of the above described methods and synthesizing and/or formulating the compound identified in step (b) or a derivative or homologue thereof in a pharmaceutically acceptable form. The therapeutically useful compounds identified according to the method of the invention may be formulated and administered to a patient as discussed above. For uses and therapeutic doses determined to be appropriate by one skilled in the art see infra.

Furthermore, the present invention relates to a method for the preparation of a pharmaceutical composition comprising the steps of the above-described methods; and formulating a drug or pro-drug in the form suitable for therapeutic application and preventing or ameliorating the disorder of the subject diagnosed in the method of the invention.

Drugs or pro-drugs after their in vivo administration are metabolized in order to be eliminated either by excretion or by metabolism to one or more active or inactive metabolites (Meyer, J. Pharmacokinet. Biopharm. 24 (1996), 449–459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323–329).

In a preferred embodiment of the method of the present invention said drug or prodrug is a derivative of a medicament as defined hereinbefore.

In a still further embodiment the present invention relates to an inhibitor identified or obtained by the method described hereinbefore. Preferably, the inhibitor binds specifically to the variant hPXR protein of the invention. The antibodies, nucleic acid molecules and inhibitors of the present invention preferably have a specificity at least substantially identical to binding specificity of the natural ligand or binding partner of the hPXR protein of the invention. An antibody or inhibitor can have a binding affinity to the hPXR protein of the invention of at least $10^5$ $M^{-1}$, preferably higher than $10^7$ $M^{-1}$ and advantageously up to $10^{10}$ $M^{-1}$ in case hPXR activity should be repressed. Hence, in a preferred embodiment, a suppressive antibody or inhibitor of the invention has an affinity of at least about $10^{-7}$ M, preferably at least about $10^{-9}$ M and most preferably at last about $10^{-11}$ M.

Furthermore, the present invention relates to the use of an oligo- or polynucleotide for the detection of a polynucleotide of the invention and/or for genotyping of corresponding individual hPXR alleles. Preferably, said oligo- or polynucleotide is a polynucleotide or a nucleic acid molecule of the invention described before.

In a particular preferred embodiment said oligonucleotide is about 15 to 50, preferably 20 to 40, more preferably 20 to 30 nucleotides in length and comprises the nucleotide sequence of any one of SEQ ID NOS: 1 to 165 or a complementary sequence.

Hence, in a still further embodiment, the present invention relates to a primer or probe consisting of an oligonucleotide as defined above. In this context, the term "consisting of" means that the nucleotide sequence described above and employed for the primer or probe of the invention does not have any further nucleotide sequences of the hPXR gene immediately adjacent at its 5' and/or 3' end. However, other moieties such as labels, e.g., biotin molecules, histidin flags, antibody fragments, colloidal gold, etc. as well as nucleotide sequences which do not correspond to the hPXR gene may be present in the primer and probes of the present invention. Furthermore, it is also possible to use the above described particular nucleotide sequences and to combine them with other nucleotide sequences derived from the hPXR gene wherein these additional nucleotide sequences are interspersed with moieties other than nucleic acids or wherein the nucleic acid does not correspond to nucleotide sequences of the hPXR gene. Furthermore, it is evident to the person skilled in the art that the oligonucleotide can be modified, for example, by thio-phosphate-backbones and/or base analogs well known in the art (Flanagan, Proc. Natl. Acad. Sci. USA 96 (1999), 3513–8; Witters, Breast Cancer Res. Treat. 53 (1999), 41–50; Hawley, Antisense Nucleic Acid Drug Dev. 9 (1999), 61–9; Peng Ho, Brain Res. Mol. Brain Res. 62 (1998), 1–11; Spiller, Antisense Nucleic Acid Drug Dev. 8 (1998), 281–93; Zhang, J. Pharmacol. Exp. Ther. 278 (1996), 971–9; Shoji, Antimicrob. Agents Chemother. 40 (1996), 1670–5; Crooke, J. Pharmacol. Exp. Ther. 277 (1996), 923–37).

In addition, the present invention relates to the use of an antibody or a substance capable of binding specifically to the gene product of an hPXR gene for the detection of the variant hPXR protein of the invention, the expression of a molecular variant hPXR gene comprising a polynucleotide of the invention and/or for distinguishing hPXR alleles comprising a polynucleotide of the invention.

Moreover, the present invention relates to a composition, preferably pharmaceutical composition comprising the antibody, the nucleic acid molecule, the vector or the inhibitor of the present invention, and optionally a pharmaceutically acceptable carrier. These pharmaceutical compositions comprising, e.g., the inhibitor or pharmaceutically acceptable salts thereof may conveniently be administered by any of the routes conventionally used for drug administration, for instance, orally, topically, parenterally or by inhalation. Acceptable salts comprise acetate, methylester, HCl, sulfate, chloride and the like. The compounds may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. Furthermore, the use of pharmaceutical compositions which comprise antisense-oligonucleotides which specifically hybridize to RNA encoding mutated versions of a hPXR gene according to the invention or which comprise antibodies specifically recognizing mutated hPXR protein but not or not substantially the functional wild-type form is conceivable in cases in which the concentration of the mutated form in the cells should be reduced.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients at the wrong dose.

Furthermore, the present invention relates to a diagnostic composition or kit comprising any one of the aforedescribed polynucleotides, vectors, host cells, variant hPXR proteins, antibodies, inhibitors, nucleic acid molecules or the corresponding vectors of the invention, and optionally suitable means for detection.

The kit of the invention may contain further ingredients such as selection markers and components for selective media suitable for the generation of transgenic cells and animals. The kit of the invention may advantageously be used for carrying out a method of the invention and could be, inter alia, employed in a variety of applications, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or diagnostic compositions may be used for methods for detecting expression of a mutant form of hPXR gene in accordance with any one of the above-described methods of the invention, employing, for example, immunoassay techniques such as radioimmunoassay or enzymeimmunoassay or preferably nucleic acid hybridization and/or amplification techniques such as those described herein before and in the examples.

Some genetic changes lead to altered protein conformational states. For example, some variant hPXR proteins may possess a tertiary structure that renders them far less capable of facilitating drug metabolization and transcription initiation, respectively. Restoring the normal or regulated conformation of mutated proteins is the most elegant and specific means to correct these molecular defects, although it is difficult. Pharmacological manipulations thus may aim at restoration of wild-type conformation of the protein. Thus, the polynucleotides and encoded proteins of the present invention may also be used to design and/or identify molecules which are capable of activating the wild-type function of a hPXR gene or protein.

In another embodiment the present invention relates to the use of a drug or prodrug for the preparation of a pharmaceutical composition for the treatment or prevention of a disorder diagnosed by the method described hereinbefore.

Furthermore, the present invention relates to the use of an effective dose of a nucleic acid sequence encoding a functional and expressible wild type hPXR protein for the preparation of a pharmaceutical composition for treating, preventing and/or delaying a disorder diagnosed by the method of the invention. A gene encoding a functional and expressible hPXR protein can be introduced into the cells which in turn produce the protein of interest. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534–539; Schaper, Circ. Res. 79 (1996), 911–919; Anderson, Science 256 (1992), 808–813; Isner, Lancet 348 (1996), 370–374; Muhlhauser, Circ. Res. 77 (1995), 1077–1086; Wang, Nature Medicine 2 (1996), 714–716; WO94/29469; WO 97/00957 or Schaper, Current Opinion in Biotechnology 7 (1996), 635–640, and references cited therein. The gene may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

As is evident from the above, it is preferred that in the use of the invention the nucleic acid sequence is operatively linked to regulatory elements allowing for the expression and/or targeting of the hPXR protein to specific cells. Suitable gene delivery systems that can be employed in accordance with the invention may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726–2729). Standard methods for transfecting cells with recombinant DNA are well known to those skilled in the art of molecular biology, see, e.g., WO 94/29469; see also supra. Gene therapy may be carried out by directly administering the recombinant DNA molecule or vector of the invention to a patient or by transfecting cells with the polynucleotide or vector of the invention ex vivo and infusing the transfected cells into the patient.

In a preferred embodiment of the uses and methods of the invention, said disorder is cancer.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. An overview of patent information in biotechnology and a survey of relevant sources of patent information useful for retrospective searching and for current awareness is given in Berks, TIBTECH 12 (1994), 352–364.

The pharmaceutical and diagnostic compositions, uses, methods of the invention can be used for the diagnosis and treatment of all kinds of diseases hitherto unknown as being related to or dependent on variant hPXR genes. The compositions, methods and uses of the present invention may be desirably employed in humans, although animal treatment is also encompassed by the methods and uses described herein.

BRIEF DESCRIPTION OF THE FIGURES

FIG. 4: Genomic sequences and polymorphisms in the hPXR genes. Primers used for the amplification and sequencing (Table 3), as well as splice sites are underlined. Thick underlined are polymorphic sites and they are shown as the wild-type and variant base, separated by an arrow.

FIG. 6: LS174T cells were co-transfected with the promoter artificial hPXR dependent reporter gene pGL3(DR3) 3Tk(−105), pCMVβ and expression plasmids for hPXR variants, as indicated. Cells were treated for 42 hours with 10 µM rifampicin or 0.1% DMSO, then harvested and analyzed for luciferase and β-galactosidase activities. Data are shown as mean value ±SD. The activity of each hPXR variant in the presence of DMSO only was taken as 1 (A, B) or 100% (C). A) The effect of hPXR variants following 10 µM rifampicin. B) The effect of hPXR variants in the absence of exogenous inducers.

The invention will now be described by reference to the following examples which are merely illustrative and are not to be construed as a limitation of the scope of the present invention.

EXAMPLES

Example 1

Figure 1:
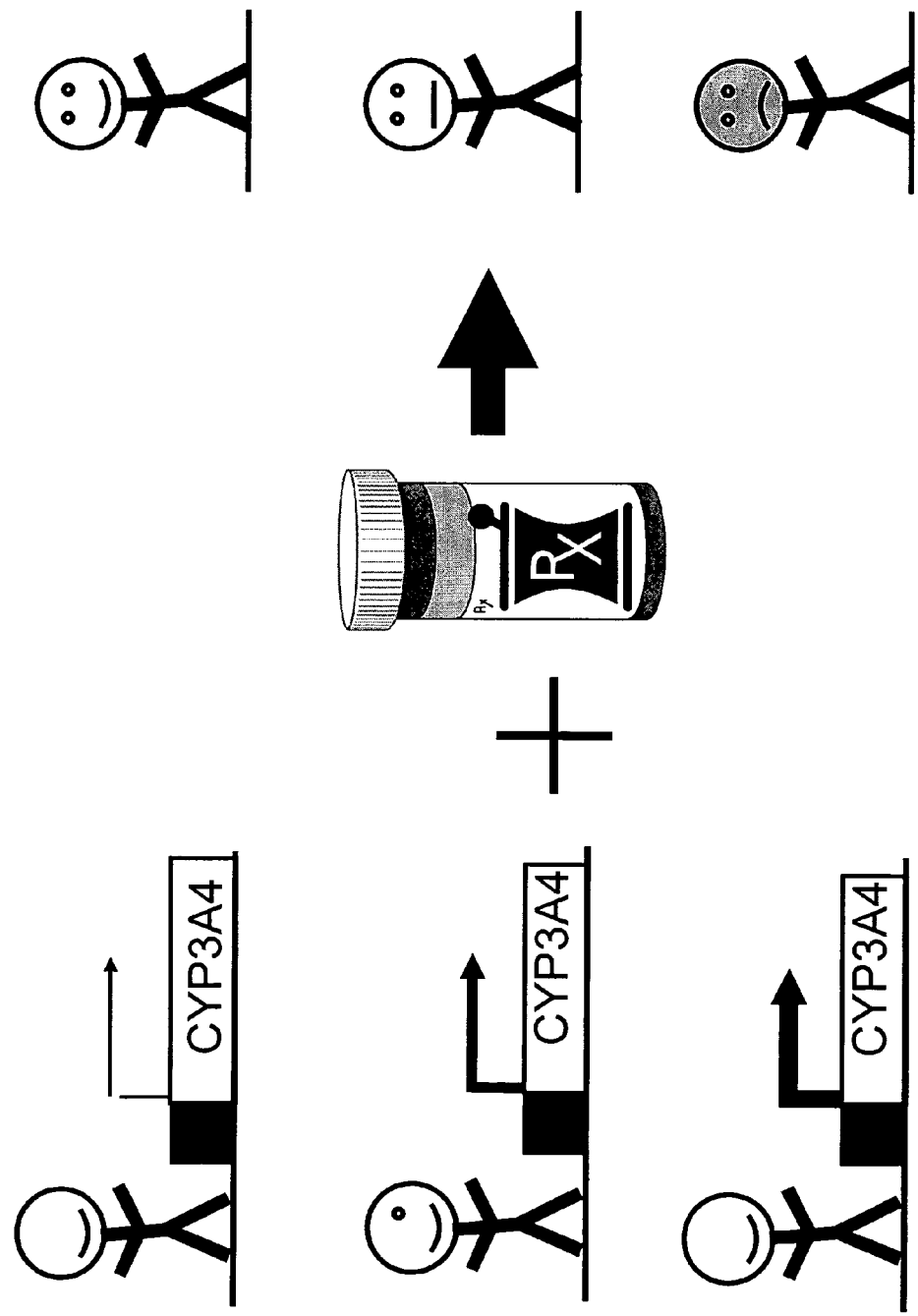
FIG. 1: Differences in the genetic makeup influence the efficacy and safety of drug treatment.
Figure 2:
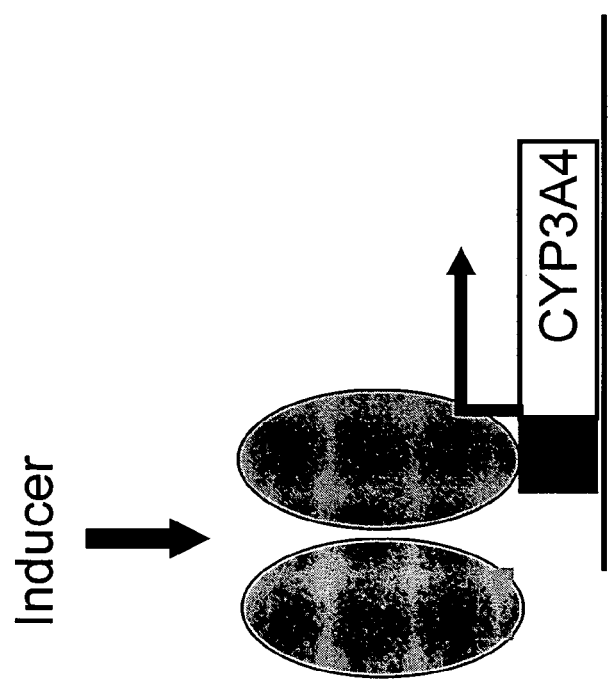
FIG. 2: A current model of the regulation of CYP3A4 by hPXR.
Figure 3:
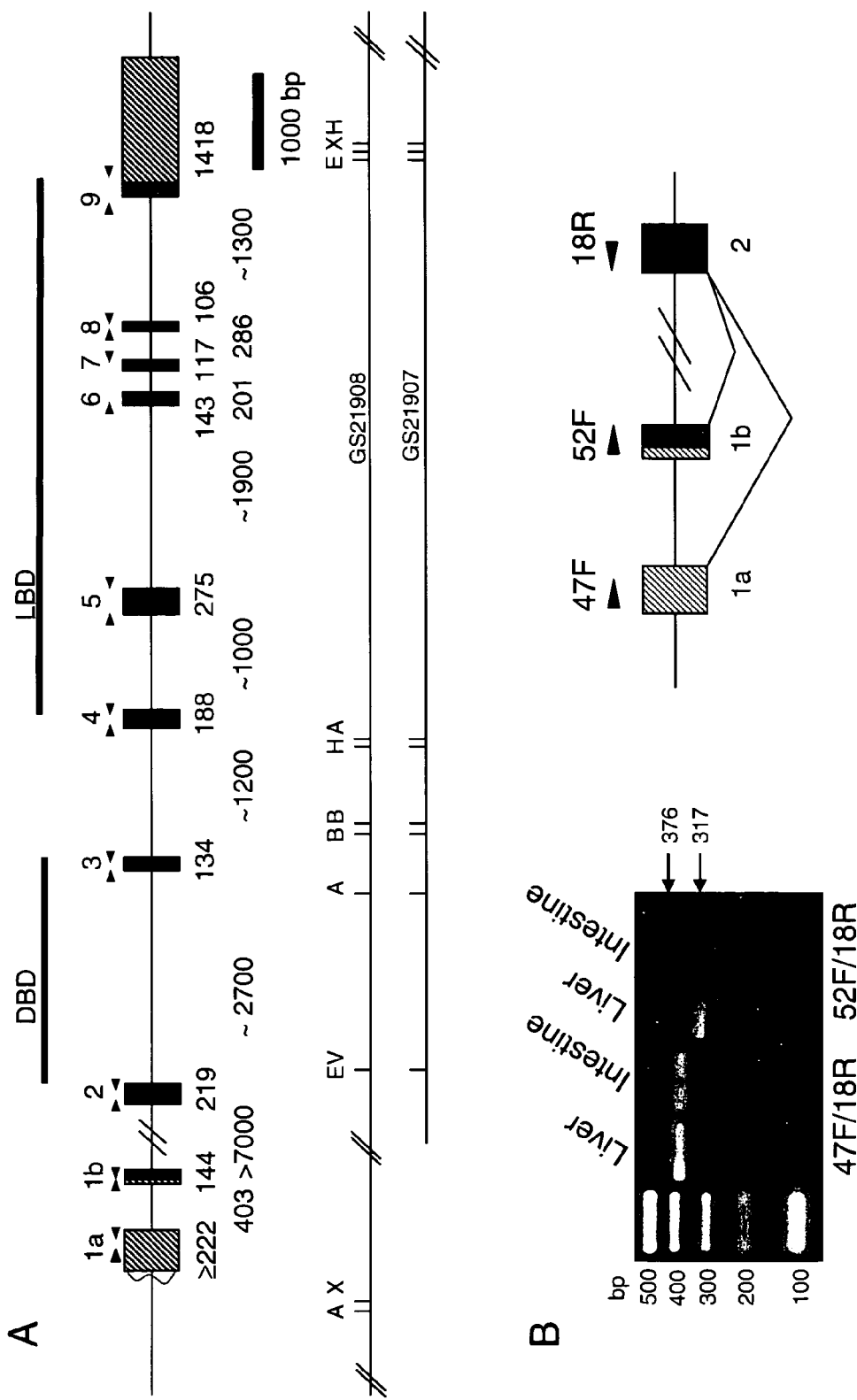
FIG. 3: A) Structure of the hPXR gene. Coding regions are indicated as filled rectangles, non-coding 5' and 3' untranslated regions as dashed rectangles. Arrowheads represent the positions of oligonucleotides used to screen the coding region of the gene. The horizontal bars labeled DBD and LBD mark the location of the DNA binding domain and ligand binding domain, respectively. The horizontal lines at the bottom indicate human genomic BAC clones GS21907 and GS21908 including the restriction sites for ApaI (A), BglII (B), EcoRI (E), EcoRV (EV), HindIII (H) and XbaI (X). B) Differential expression of exons 1a and 1b of hPXR in the liver and intestine as investigated by PCR amplification of tissue-derived cDNAs. Primers used for amplification are indicated underneath the agarose gel and by arrows in exons 1a, 1b and 2.

Genomic Organization and Oligonucleotides for the Amplification of the Coding Regions of hPXR The genomic structure of hPXR was determined by sequencing PCR fragments generated with oligonucleotides located in two neighboring exons as well as by direct sequencing of an hPXR-containing BAC (Genome Systems GS21908). Comparison between the obtained genomic and GenBank cDNA sequences (gi 3769538, gi 3769536, gi 5852062, gi 5852066, gi 3511137) revealed that the gene consists of 10 exons and 9 introns and spans at least 20 kb of genomic DNA. The approximate size of intron 1b is estimated to be >7 kb (FIG. 3, Tables 1 and 2), based on restriction mapping of BACs GS21908 and GS21907 followed by hybridization with several probes derived from the gene. Exon and intron sizes as well as sequences at exon-intron boundaries are given in Table 2.

Sequence and gene expression analyses revealed that exons 1a and 1b are utilized as alternative 5' ends of hPXR transcripts (Bertilsson, Proc Natl Acad Sci USA 95 (1998), 12208–13). Thus, intron 1a lacks a 3' consensus splice site (not shown). The two exons are differentially expressed in tissues where hPXR is transcribed. Exon 1a is expressed both in liver and small intestine whereas exon 1b is only expressed in the liver (FIG. 3B).

Example 2

Isolation of Genomic DNA, Amplification, Purification and Sequencing of hPXR Gene Fragments Genomic DNA was isolated using standard techniques from blood or liver samples obtained from Caucasians or Black Africans. Conditions for the amplification of hPXR gene fragments by PCR are given in Table 3, respectively. The complete sequences of the amplicons are given in FIG. 4. The quality of amplicons was routinely checked by agarose gel electrophoresis. The fragments were then processed through PCR purification columns (Qiagen) which remove all the components of the PCR that could otherwise interfere with the subsequent sequencing reaction.

The sequencing reaction was performed using the dye-terminator method and the samples were then resolved on polyacrylamide gels (Perkin-Elmer 377 and 3700 sequencing machines). Both strands were routinely sequenced to assure high accuracy of the results and the detection of heterozygotes. The sequences were visually inspected for their quality and then analyzed for the presence of polymorphisms using the PHRED/PHRAP/POLYPHRED/CONSED software package (University of Washington, Seattle, USA).

Example 3

Polymorphisms in the hPXR Gene

The coding region of hPXR, parts of the 5' and 3' UTR as well as some intron sequences flanking the gene's exons were amplified by PCR from genomic DNA and sequenced (Table 3). The screen was carried out on between 300 and 418 Caucasian, and 54 to 74 African chromosomes (Tables 4 and 5). Altogether, 28 variants were found in the samples screened (Tables 4 and 5). Nine variants were found only in Caucasians, 14 were exclusive for Africans, whereas only five were common for both ethnic groups. Thirteen variants are located within the protein-coding sequence, 8 in flanking intron sequences and seven in the 5' or 3' UTR. Among the 13 variants found in the protein-coding region, six affect the hPXR protein sequence, whereas 7 are silent (Tables 4 and 5). Three protein variants (E18K, P27S and G36R) are located in exon 2. Two of them (E18K and P27S) were identified exclusively in Africans. The most frequent protein polymorphism (P27S) occurs in 14.9% African chromosomes. The G36R variant is found only in Caucasians and it has an allelic frequency of 3%. 0.5% Caucasians are heterozygous for the V140M variant, and 2.7% Africans for the D163G variant. 3.1% Africans are heterozygous for the A370T variant. No mutations were detected within the conserved splice sites (AG and GT). Altogether, the protein-coding sequence of hPXR found in a majority of Caucasians and Africans is identical to the reported cDNA sequence (gi 3769538) except for position 112, wherein an A is replaced by a G in all samples analyzed.

Example 4

Functional Characterization of hPXR Protein Variants

Figure 5:
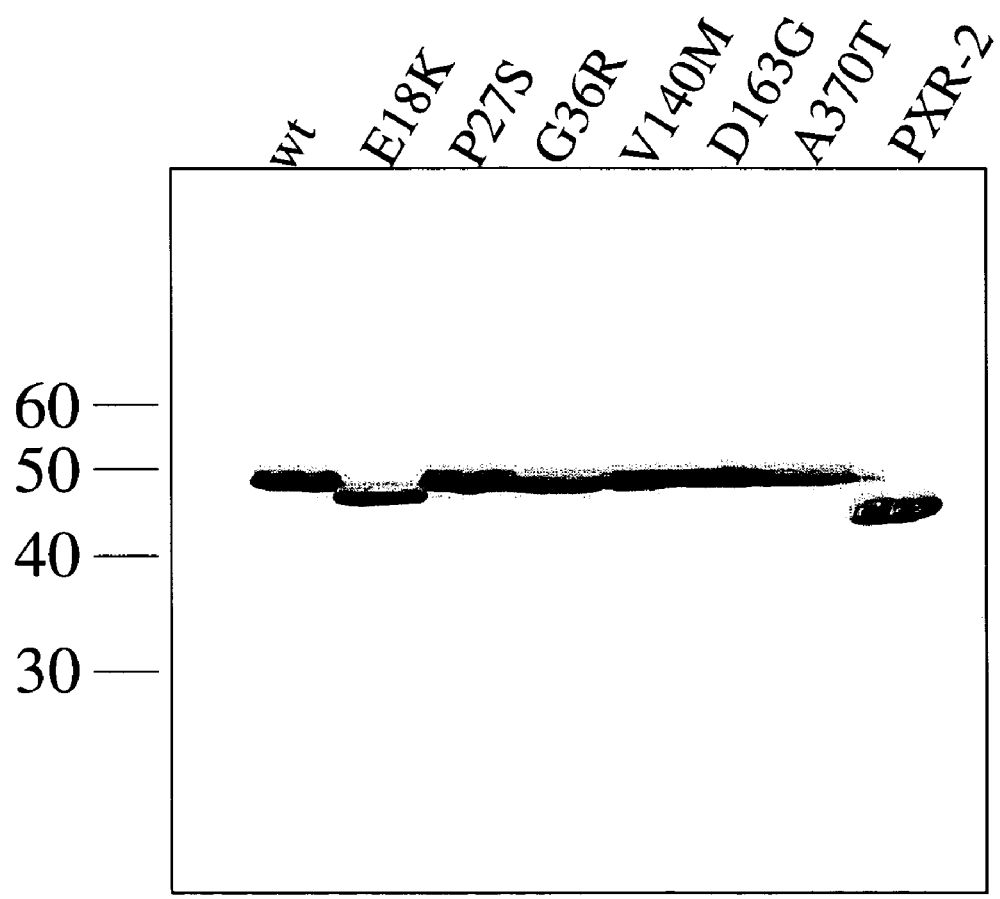
FIG. 5: Western Blot analysis of total cellular protein of COS-1 cells transiently transfected with 5 µg of expression plasmids for wild-type or variant hPXR proteins. Protein amounts were adjusted according to transfection efficiency as estimated by the activity of the β-galactosidase co-transfected into the cells. Blots were probed with a hPXR-specific antibody. Molecular weight markers (in kD) are shown on the left.

In the following, we investigated the effect of the missense hPXR mutations on the expression and activity of the hPXR protein. We also investigated the effect of the hPXR-2 splice variant which results from a cryptic splice acceptor site within exon 5 leading to a deletion of 37 amino acids from the ligand-binding domain of hPXR (Dotzlaw, Clin Cancer Res 5 (1999), 2103–7). To this end, we constructed eukaryotic expression plasmids for all six hPXR protein variants and for the hPXR-2 deletion variant. The sequence of the protein encoded by the "wild-type" construct is identical to that found in most Caucasians and Africans. Western Blot analysis of COS-1 cells transiently transfected with these plasmids showed that all variants directed the expression of similar amounts of protein (FIG. 5). The apparent sizes of the variants were in agreement with the calculated molecular weight of hPXR (49.7 kD) and hPXR-2 (45.7 kD) with the exception of the E18K variant, which showed an apparent molecular weight of 47–48 kD (FIG. 5).

The functional consequences of the protein variants were investigated in LS174T cells. LS174T cells were first co-transfected with wild-type or variant hPXR expression plasmids together with the hPXR-dependent promoter-reporter gene plasmid pGL3(DR3)₃TK(–105). The plasmid contains three copies of the DR3 motif of the CYP3A23 promoter, which has been shown to be a hPXR response element (Kliewer, Cell (1998), 73–82), inserted upstream of a minimal thymidine kinase promoter and luciferase. The cells were treated with the xenobiotic rifampicin, a known activator of human hPXR (Blumberg, Genes Dev (1998), 3195–3205; Lehmann, J Clin Invest (1998), 1016–1023). FIG. 6A shows that variants E18K, P27S and G36R stimulated transcription of the reporter gene in this assay as efficiently as wild type hPXR following rifampicin treatment. In contrast, hPXR-mediated transcriptional activation was impaired in V140M, D163G and hPXR-2 variants. Upon treatment with rifampicin, V140M, and D163G variants exhibit only 50% of wild type activity, whereas hPXR-2 had only an activity of approximately 25% (FIG. 6A). A370T also showed a slightly impaired transcriptional activation after treatment with rifampicin, but this reduction was not significant in said series of experiments and needs to be confirmed by additional experiments or in another assay system (FIG. 6A). As summarized in FIG. 6B in the absence of added hPXR activators, the variants E18K, P27S and G36R exhibited lower basal activity than wild type hPXR, whereas V140M and A370T showed an enhanced basal activity (130% or 207%, respectively). In contrast, D163G and hPXR-2 showed a strongly reduced basal activity (approximately 10% of wild type). Changes in basal activity of variants are independent from activator-dependent activity. Whereas V140M and A370T had a higher basal activity, but a reduced or equal activity upon activation of the mutant hPXR, D163G and hPXR-2 both had a lower basal activity as well as a reduced activity upon activation.

TABLE 1

Oligonucleotides used to determine the structure and exon/intron boundaries of the hPXR gene.

| Name | Position | Sequence (5'–3') |
|---|---|---|
| hPXR1F | exon 4 | TCATGTCCGACGAGGCCG |
| hPXR4F | exon 5/6 | CCCACATGGCTGACATGT |
| hPXR5F | exon 7 | CCCATCGAGGACCAGATC |
| hPXR6R | exon 7 | GTCTTCCAAGCAGTAGGA |
| hPXR7R | exon 8 | CAGCATGGGCTCCAGTAG |
| hPXR10R | exon 9a | CCTGTGATGCCGAACAAC |
| hPXR11F | exon 9 | CATTGAATGCAATCGGCC |
| hPXR12R | exon 9a | GCTCTTGGCAGTGTCCAT |
| hPXR15F | exon 2 | GGAAAGCCCAGTGTCAAC |
| hPXR16F | exon 3 | CCATGAAACGCAACGCCC |
| hPXR18R | exon 2 | CCTTGCATCCTTCACATG |
| hPXR19R | exon 3 | CATGCCGCTCTCCAGGCA |
| hPXR20R | exon 4 | CGGCCTCGTCGGACATGA |
| hPXR21R | exon 5/6 | ACATGTCAGCCATGTGGG |
| hPXR47F | exon 1b | CAAGCCAAGTGTTCACAGTG |
| hPXR48R | exon 1b | CACTGTGAACACTTGGCTTG |
| hPXR52F | exon 1a | CAAGGACAGCAGCATGACAGTCAC |
| hPXR54R | exon 1a | AGCCAACTCAGCCGCAGC |

Fifty ng of genomic DNA was added to a reaction mix (total volume 30 or 50 µl) containing 1× PCR buffer (Q=Qiagen, Cat. Nr. 1005479, or B2=Boehringer (currently Roche) Expand Long Template PCR Buffer number 2, Cat. Nr. 1742655), 0.25 µM each oligonucleotide, 200 µM dNTPs, and 1 U of Taq polymerase (Qiagen). Amplifications were performed on a RoboCycler Gradient 96 (Stratagene) with an initial denaturation step of 2 min. at 94° C. followed by 32 amplification cycles of denaturation (40 sec., 94° C.), annealing (45 sec., temperatures 56–60° C.), and extension (60–150 sec., 72° C.). This was followed by a final extension step 5 min., 72° C. All sequencing reactions were performed on a GeneAmp PCR System 9700 (Perkin-Elmer) using a dye-terminator DNA sequencing kit (Perkin-Elmer, Cat. Nr. 4303154), according to manufacturer's instructions.

TABLE 2

Exon-intron organization of the hPXR gene*.

| Exon number | Exon size (bp) | Sequence at exon-intron junction 5' splice site | Sequence at exon-intron junction 3' splice site | Intron size (kb) |
|---|---|---|---|---|
| 1a | ≧222 | AAGCAG gtatgg . . . | — | 0.403 |
| 1b | 144 | AAACCA gtgagt . . . | . . . ttctag TCCAAG | ≧7.0 |
| 2 | 219 | TTTCAG gtagag . . . | . . . tcacag GAGGGC | ~2.7 |
| 3 | 134 | AGGAGA gtgagc . . . | . . . ctgcag TGATCA | ~1.2 |
| 4 | 188 | TTCCGG gtagga . . . | . . . tcctag CTGCCA | ~1.0 |
| 5 | 275 | CTTCAG gtagga . . . | . . . tgccag GGACTT | ~1.9 |
| 6 | 143 | CTGCAG gtgccc . . . | . . . ccacag GTGGCT | 0.201 |
| 7 | 117 | CCCCAG gtgagg . . . | . . . ctccag ACCGCC | 0.286 |
| 8 | 106 | TCATAG gtgagc . . . | . . . atgcag GTTCTT | ~1.3 |
| 9 | ≧1418 | | | |

*Exon sequences are shown in capital letters, intron sequences in small letters. No 3' splice site is indicated in intron 1 due to the alternative usage of exons 1a and 1b in hPXR transcripts.

TABLE 3 hPXR polymorphism screen: oligonucleotide sequences, amplification conditions and fragment size.

| Exon | Upstream Oligonucleotide Name | Upstream Oligonucleotide Sequence (5'-3') | Downstream Oligonucleotide Name | Downstream Oligonucleotide Sequence (5'-3') | Ann. Temp (° C.) | Buffer | Product Size (bp) |
|---|---|---|---|---|---|---|---|
| 1a | HPXR57F | TCAAGTGCTGGACTTGGGAC | HPXR58R | CCCACTATGATGCTGACCTC | 53 | B2 | 460 |
| 1b | HPXR82F | CACATACAACCAGCTCCCTG | HPXR60R | CCACATGCAGGCAAGACTC | 58 | Q | 345 |
| 2 | HPXR41F | CTGAGGCCTCTACACATC | HPXR40R | AGGCCCTGAGATGTTACC | 55 | Q | 345 |
| 3 | HPXR53F | CTGGGACGCAAAGGCTAGTG | HPXR46R | CCTGTTGCACACGGACAC | 57 | Q* | 417 |
| 4 | HPXR81F | TAACGGCTTCTGCTGCCTTG | HPXR80R | AGCTCTCCAAATCTACCCTC | 58 | Q | 423 |
| 5 | HPXR32F | CTGAGTTGGGACCTGTCT | HPXR35R | CCAGGCCCTTTGAACCTC | 58 | B2 | 415 |
| 6 & 7 | HPXR36F | CTGCTGGTGCCGGCCTGT | HPXR33R | GACTGGGACCTTCCCTGG | 60 | B2 | 598 |
| 8 | HPXR34F | GAGCAATGCCCTGACTCT | HPXR26R | CCCTCTGGCCATGAAGTC | 60 | B2 | 271 |
| 9 | HPXR30F | TGCTTGTGCAGCCTCAGA | HPXR12R | GCTCTTGGCAGTGTCCAT | 60 | B2 | 324 |

Fiftying of genonmic DNA was added to a reaction mix (total volume 30 or 50 μl) containing 1 × PCR buffer (Q = Qiagen, Cat. Nr. 1005479, or B2 = Boehringer (currently Roche) Expand Long Template PCR Buffer number 2, Cat. Nr. 1742655), 0.25 μM each oligonucleotide, 200 μM dNTPs, and 1 U of Taq polymerase (Qiagen). Amplifications were performed on a RoboCycler Gradient 96 (Stratagene) with an initial denaturation step of 2 min. at 94° C. followed by 32–34 amplification cycles of denaturation (40 sec., 94° C.) annealing (45 sec., temperatures given above), and extension (60 sec., 72° C.). This was followed by a final extension step 5 min., 72° C. All sequencing reactions were performed on a GeneAmp PCR System 9700 (Perkin-Elmer) using a dye-terminator DNA sequencing kit (Perkin-Elmer, Cat. Nr. 4303154), according to manufactures's instructions.
*5% DMSO was added and Hot Star Taq Qiagen.

TABLE 4

Positions, sequence context, and frequencies of hPXR variants in different populations

| hPXR variant | Variant | Nucleotide sequence Reference (5'-3') | Nucleotide sequence Variant | Genetic element | Predicted effect |
|---|---|---|---|---|---|
| M20 | c. 1 − 201G > A | ATCTCGGCCTC | ATCTCAGCCTC | 5'UTR (Ex1a) | |
| M1 | c. 1 − 131C > A | CTGAACAAGGC | CTGAAAAAGGC | 5'UTR (Ex1a) | |
| M21 | c. 1 − 57G > T | CCAGGGGAGAA | CCAGGTGAGAA | 5'UTR (Ex1a) | |
| M2 | c. 1 − 100T > G* | GACTGTGGGAG | GACTGGGGGAG | Intron 1b | |
| M3 | c. 1 − 20delC* | CCCCCCTGAGG | CCCCC-TGAGG | 5'UTR (Ex1b) | |
| M6 | c. 1 − 42T > C | TTCTCTGTGGT | TTCTCCGTGGT | Intron 1b | |
| M5 | c. 52G > A | ACTGTGAGGAC | ACTGTAAGCGC | Exon 2 | E18K |
| M7 | c. 79C > T | GAAAGCCCAGT | GAAAGTCCAGT | Exon 2 | P27S |
| M4 | c. 106G > A | AAGTCGGAGGT | AAGTCAGAGGT | Exon 2 | G36R |
| M22 | c. 198 − 29C > T | TGCATCCCCCC | TGCATTCCCCC | Intron 2 | |

TABLE 4-continued

Positions, sequence context, and frequencies of hPXR variants in different populations

| | | | | | |
|---|---|---|---|---|---|
| M8  | c. 225G > C      | CGGCTGAGGTG | CGGCTCAGGTG | Exon 3   | silent |
| M23 | c. 315C > T      | GAGAGCGGCAT | GAGAGTGGCAT | Exon 3   | silent |
| M9  | c. 331 + 72T > G | GTGTGTGCATG | GTGTGGGCATG | Intron 3 | |
| M10 | c. 418G > A      | TGGGAGTGCAG | TGGGAATGCAG | Exon 4   | V140M |
| M11 | c. 488A > G      | CTTTGACACTA | CTTTGGCACTA | Exon 4   | D163G |
| M12 | c. 492T > C      | GACACTACCTT | GACACCACCTT | Exon 4   | silent |
| M13 | c. 543C > T      | AGTGGCTGCGA | AGTGGTTGCGA | Exon 5   | silent |
| M14 | c. 696C > T      | AGTGGCGGGAA | AGTGGTGGGAA | Exon 5   | silent |
| M24 | c. 834G > A      | AAGGGGGCCGC | AAGGGAGCCGC | Exon 6   | silent |
| M15 | c. 937 + 99G > A | TGGCAGGGCAG | TGGCAAGGCAG | Intron 6 | |
| M16 | c. 938 − 73A > G | ACAAGATATTG | ACAAGGTATTG | Intron 6 | |
| M17 | c. 938 − 17C > T | TCCATCCTGTT | TCCATTCTGTT | Intron 6 | |
| M25 | c. 984C > T      | CACTACATGCT | CACTATATGCT | Exon 7   | silent |
| M26 | c. 1054 + 36C > T| CCCCCCAGCCT | CCCCTAGCCT  | Intron 7 | |
| M27 | c. 1108G > A     | AATTCGCCATT | AATTCACCATT | Exon 8   | A370T |
| M18 | c. 1160 + 43G > A| GTGAGGGAGCC | GTGAGAGAGCC | Intron 8 | |
| M19 | c. 1308G > A     | TGAGCGGCTGC | TGAGCAGCTGC | 3'UTR    | |
| M28 | c. 1320G > A     | CTTGGGTGACA | CTTGGATGACA | 3'UTR    | |

| | | Caucasians | | | Africans | | |
|---|---|---|---|---|---|---|---|
| | | Genotype frequency (%) | | Variant allele frequency (%) | | Genotype frequency (%) | Variant allele frequency (%) |
| hPXR variant | Chr. (N) | Hetero-zygous | Homo-zygous | quency (%) | Chr. (N) | Hetero-zygous Homo-zygous | quency (%) |
| M20 | 300 | 0.0  | 0.0  | 0.0  | 56 | 3.6  | 0.0  | 1.8  |
| M1  | 300 | 50.7 | 35.3 | 60.7 | 56 | 14.3 | 0.0  | 7.1  |
| M21 | 300 | 0.0  | 0.0  | 0.0  | 56 | 3.6  | 0.0  | 1.8  |
| M2  | 300 | 1.3  | 0.0  | 0.7  | 60 | 0.0  | 0.0  | 0.0  |
| M3  | 300 | 50.0 | 36.0 | 61.0 | 60 | 63.3 | 33.3 | 65.0 |
| M6  | 300 | 0.0  | 0.0  | 0.0  | 74 | 10.8 | 0.0  | 5.4  |
| M5  | 300 | 0.0  | 0.0  | 0.0  | 74 | 2.7  | 0.0  | 1.4  |
| M7  | 300 | 0.0  | 0.0  | 0.0  | 74 | 24.3 | 2.7  | 14.9 |
| M4  | 300 | 6.0  | 0.0  | 3.0  | 74 | 0.0  | 0.0  | 0.0  |
| M22 | 300 | 0.0  | 0.0  | 0.0  | 62 | 2.7  | 0.0  | 11.3 |
| M8  | 300 | 0.7  | 0.0  | 0.3  | 62 | 0.0  | 0.0  | 0.0  |
| M23 | 300 | 0.0  | 0.0  | 0.0  | 62 | 12.9 | 0.0  | 6.5  |
| M9  | 300 | 14.7 | 0.0  | 7.3  | 62 | 48.4 | 3.2  | 27.4 |
| M10 | 418 | 0.5  | 0.0  | 0.2  | 74 | 0.0  | 0.0  | 0.0  |
| M11 | 418 | 0.0  | 0.0  | 0.0  | 74 | 2.7  | 0.0  | 1.4  |
| M12 | 418 | 0.0  | 0.0  | 0.0  | 74 | 18.9 | 0.0  | 9.5  |
| M13 | 300 | 2.0  | 0.0  | 1.0  | 54 | 0.0  | 0.0  | 0.0  |
| M14 | 300 | 3.3  | 0.7  | 2.3  | 54 | 0.0  | 0.0  | 0.0  |
| M24 | 370 | 0.0  | 0.0  | 0.0  | 56 | 7.1  | 0.0  | 3.6  |
| M15 | 370 | 0.5  | 0.0  | 0.3  | 62 | 0.0  | 0.0  | 0.0  |
| M16 | 370 | 0.5  | 0.0  | 0.3  | 56 | 3.6  | 0.0  | 1.8  |
| M17 | 370 | 33.0 | 3.8  | 20.3 | 56 | 64.3 | 14.3 | 46.4 |
| M25 | 370 | 0.0  | 0.0  | 0.0  | 56 | 3.6  | 0.0  | 1.8  |
| M26 | 370 | 0.0  | 0.0  | 0.0  | 56 | 3.6  | 0.0  | 1.8  |
| M27 | 312 | 0.0  | 0.0  | 0.0  | 64 | 3.1  | 0.0  | 1.6  |
| M18 | 312 | 0.6  | 0.0  | 0.3  | 64 | 0.0  | 0.0  | 0.0  |
| M19 | 300 | 0.7  | 0.0  | 0.3  | 64 | 0.0  | 0.0  | 0.0  |
| M28 | 300 | 0.0  | 0.0  | 0.0  | 60 | 10.0 | 3.3  | 8.3  |

The nomenclature of the variants (column two) is based on Antonarakis and the Nomenclature Working Group (Antonarakis, Hum Mutat 11 (1998), 1–3). As the translation initiation site the CTG with the C at position 280 of the cDNA (gi 3769538) is numbered +1. The nucleotide 5' to +1 is numbered −1. SNPs that are located in introns are indicated by the number of nucleotides upstream (+) or downstream (−) the nucleotide position of exons defined in this paper (Table 1). 28 variants were identified. The variant position is indicated in bold. A 1 bp deletion is indicated by a slash. The number of samples analyzed is N/2. N = number of chromosomes analyzed, Ex = Exon; *The reference sequence is gi 3769536. The A (+1) of the start codon ATG is at position 60 of the cDNA.

TABLE 5

Genetic variants of hPXR

| Position | wt sequence (5'-3') | mut sequence (5'-3') |
|---|---|---|
| exon 1a | F: ATCTCGGCCTC | F: ATCTCAGCCTC |
|  | R: GAGGCCGAGAT | R: GAGGCTGAGAT |
| exon 1a | F: CTGAACAAGGC | F: CTGAAAAAGGC |
|  | R: GCCTTGTTCAG | R: GCCTTTTTCAG |
| exon 1a | F: CCAGGGGAGAA | F: CCAGGTGAGAA |
|  | R: TTCTCCCCTGG | R: TTCTCACCTGG |
| intron 1a | F: GACTGTGGGAG | F: GACTGGGGGAG |
|  | R: CTCCCACAGTC | R: CTCCCCCAGTC |
| exon 1b | F: CCCCCCTGAGG | F: CCCCC-TGAGG |
|  | R: CCTCAGGGGGG | R: CCTCA-GGGGG |
| intron 1b | F: TTCTCTGTGGT | F: TTCTCCGTGGT |
|  | R: ACCACAGAGAA | R: ACCACGGAGAA |
| exon 2 | F: ACTGTGAGGAC | F: ACTGTAAGGAC |
|  | R: GTCCTCACAGT | R: GTCCTTACAGT |
| exon 2 | F: GAAAGCCCAGT | F: GAAAGTCCAGT |
|  | R: ACTGGGCTTTC | R: ACTGGACTTTC |
| exon 2 | F: AAGTCGGAGGT | F: AAGTCAGAGGT |
|  | R: ACCTCCGACTT | R: ACCTCTGACTT |
| intron2 | F: TGCATCCCCCC | F: TGCATTCCCCC |
|  | R: GGGGGGATGCA | R: GGGGGAATGCA |
| exon 3 | F: CGGCTGAGGTG | F: CGGCTCAGGTG |
|  | R: CACCTCAGCCG | R: CACCTGAGCCG |
| exon 3 | F: GAGAGCGGCAT | F: GAGAGTGGCAT |
|  | R: ATGCCGCTCTC | R: ATGCCACTCTC |
| intron 3 | F: GTGTCTGCATG | F: GTGTGGGCATG |
|  | R: CATGCACACAC | R: CATGCCCACAC |
| exon 4 | F: TGGGAGTGCAG | F: TGGGAATGCAG |
|  | R: CTGCACTCCCA | R: CTGCATTCCCA |
| exon 4 | F: CTTTGACACTA | F: CTTTGGCACTA |
|  | R: TAGTGTCAAAG | R: TAGTGCCAAAG |
| exon 4 | F: GACACTACCTT | F: GACACCACCTT |
|  | R: AAGGTAGTGTC | R: AAGGTGGTGTC |
| exon 5 | F: AGTGGCTGCGA | F: AGTGGTTGCGA |
|  | R: TCGCAGCCACT | R: TCGCAACCACT |
| exon 5 | F: AGTGGCGGGAA | F: AGTGGTGGGAA |
|  | R: TTCCCGCCACT | R: TTCCCACCACT |
| exon 6 | F: AAGGGGCCGC | F: AAGGGAGCCGC |
|  | R: GCGGCCCCCTT | R: GCGGCTCCCTT |
| intron 6 | F: TGGCAGGCAG | F: TGGCAAGGCAG |
|  | R: CTGCCCTGCCA | R: CTGCCTTGCCA |
| intron 6 | F: ACAAGATATTG | F: ACAAGGTATTG |
|  | R: CAATATCTTGT | R: CAATACCTTGT |
| intron 6 | F: TCCATCCTGTT | F: TCCATTCTGTT |
|  | R: AACAGGATGGA | R: AACAGAATGGA |
| exon 7 | F: CACTACATGCT | F: CACTATATGCT |
|  | R: ACCATGTAGTG | R: AGCATATAGTG |
| intron 7 | F: CCCCCCAGCCT | F: CCCCCTAGCCT |
|  | R: AGGCTGGGGGG | R: AGGCTAGGGGG |
| exon 8 | F: AATTCGCCATT | F: AATTCACCATT |
|  | R: AATGGCGAATT | R: AATGGTGAATT |
| intron 8 | F: GTGAGGGAGCC | F: GTGAGAGAGCC |
|  | R: GGCTCCCTCAC | R: GGCTCTCTCAC |
| 3'UTR | F: TGAGCGGCTGC | F: TGAGCAGCTGC |
|  | R: GCAGCCGCTCA | R: GCAGCTGCTCA |
| 3'UTR | F: CTTGGGTGACA | F: CTTGGATGACA |
|  | R: TGTCACCCAAG | R: TGTCATCCAAG |

REFERENCES (1) Daly, Toxicol Lett 102–103 (1998), 143–7
(2) Touw, Drug Metabol Drug Interact 14 (1997), 55–82
(3) Thummel, Annu Rev Pharmacol Toxicol 38 (1998), 389–430
(4) Cholerton, Trends Pharmacol Sci 13 (1992), 434–9
(5) Ketter, J Clin Psychopharmacol 15 (1995), 387–98
(6) Forrester, Proc Natl Acad Sci USA 87 (1990), 8306–10
(7) Paolini, Nature 398 (1999), 760–1
(8) Westlind, Biochem Biophys Res Commun 259 (1999), 201–5
(9) Jounaidi, Biochem Biophys Res Commun 221 (1996), 466–70
(10) Schuetz, Pharmacogenetics 4 (1994), 11–20
(11) Hunt, Clin Pharmacol Ther 51 (1992), 18–23
(12) Kashuba, Clin Pharmacol Ther 64 (1998), 269–77
(13) Peyronneau, Eur J Biochem 218 (1993), 355–61
(14) Rebbeck, J Natl Cancer Inst 90 (1998), 1225–9
(15) Felix, Proc Natl Acad Sci USA 95 (1998), 13176–81
(16) He, Biochemistry 36 (1997), 8831–9
(17) Szklarz, J Comput Aided Mol Des 11 (1997), 265–72
(18) Harlow, J Biol Chem 272 (1997), 5396–402
(19) Wang, Biochemistry 37 (1998), 12536–45
(20) Harlow, Proc Natl Acad Sci USA 95 (1998), 6636–41
(21) Domanski, Arch Biochem Biophys 350 (1998), 223–32
(22) Lehmann, J Clin Invest 102 (1998), 1016–23
(23) Bertilsson, Proc Natl Acad Sci USA 95 (1998), 12208–13
(24) Kliewer, Cell 92 (1998), 73–82
(25) Pascussi, Biochem Biophys Res Commun 260 (1999), 377–81

The invention claimed is:

1. An isolated polynucleotide encoding a variant human pregnane X receptor (hPXR) polypeptide or fragment thereof wherein the polynucleotide comprises the nucleotide sequence of SEQ ID NO: 112 and wherein the polypeptide or fragment thereof has an impaired transcriptional activity upon rifampicin treatment compared to a wild-type hPXR polypeptide.

2. A vector comprising the polynucleotide of claims 1.

3. The vector of claim 2, wherein the polynucleotide is operatively linked to expression control sequences allowing expression in prokaryotic or eukaryotic cells.

4. A host cell genetically engineered with the polynucleotide of claim 1.

5. A method for producing a molecular variant hPXR protein or fragment thereof comprising (a) culturing the host cell of claim 4; and (b) recovering said protein or fragment from the culture.

6. A method for producing cells capable of expressing a molecular variant hPXR gene comprising genetically engineering cells with the polynucleotide of claim 1.

7. A primer or probe consisting of an oligonucleotide comprising a fragment of the polynucleotide of claim 1 or a fully complementary sequence thereof wherein said fragment comprises the nucleotide sequence of SEQ ID NO: 112.

8. A composition comprising the polynucleotide of claim 1.

9. The composition of claim 8 which is a diagnostic or a composition comprising a pharmaceutically acceptable carrier, or both.

* * * * *

SEQUENCE LISTING

<160> NUMBER OF SEQ ID NOS: 185

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 1
tcatgtccga cgaggccg                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 2
cccacatggc tgacatgt                                                    18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 3
cccatcgagg accagatc                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 4
gtcttccaag cagtagga                                                    18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 5
cagcatgggc tccagtag                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 6

```
cctgtgatgc cgaacaac                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 7
cattgaatgc aatcggcc                                                    18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 8
gctcttggca gtgtccat                                                    18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 9
ggaaagccca gtgtcaac                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 10
ccatgaaacg caacgccc                                                    18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 11
ccttgcatcc ttcacatg                                                    18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 12
```
catgccgctc tccaggca                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 13
cggcctcgtc ggacatga                                                    18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 14
acatgtcagc catgtggg                                                    18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 15
caagccaagt gttcacagtg                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 16
cactgtgaac acttggcttg                                                  20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 17
caaggacagc agcatgacag tcac                                             24

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 18
agccaactca gccgcagc                                                    18

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 19
aagcaggtat gg                                                    12

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 20
aaaccagtga gt                                                    12

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 21
ttctagtcca ag                                                    12

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 22
tttcaggtag ag                                                    12

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 23
tcacaggagg gc                                                    12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 24
aggagagtga gc                                                    12

```
<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 25
ctgcagtgat ca                                                         12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 26
ttccgggtag ga                                                         12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 27
tcctagctgc ca                                                         12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 28
cttcaggtag ga                                                         12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 29
tgccagggac tt                                                         12

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 30
ctgcaggtgc cc                                                         12
```

```
<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 31
ccacaggtgg ct                                                          12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 32
ccccaggtga gg                                                          12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 33
ctccagaccg cc                                                          12

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 34
tcataggtga gc                                                          12

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 35
atgcaggttc tt                                                          12

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 36
tcaagtgctg gacttgggac                                                  20

<210> SEQ ID NO 37
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 37
cccactatga tgctgacctc                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 38
cacatacaac cagctccctg                                                  20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 39
ccacatgcag gcaagactc                                                   19

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 40
ctgaggcctc tacacatc                                                    18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 41
aggccctgag atgttacc                                                    18

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 42
ctgggacgca aaggctagtg                                                  20

<210> SEQ ID NO 43
<211> LENGTH: 18

```
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 43
cctgttgcac acggacac                                                 18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 44
taacggcttc tgctgccttg                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 45
agctctccaa atctaccctc                                               20

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 46
ctgagttggg acctgtct                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 47
ccaggccctt tgaacctc                                                 18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 48
ctgctggtgc cggcctgt                                                 18

<210> SEQ ID NO 49
<211> LENGTH: 18
<212> TYPE: DNA
```

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 49
gactgggacc ttccctgg                                    18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 50
gagcaatgcc ctgactct                                    18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 51
ccctctggcc atgaagtc                                    18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 52
tgcttgtgca gcctcaga                                    18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 53
gctcttggca gtgtccat                                    18

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 54
atctcggcct c                                           11

<210> SEQ ID NO 55
<211> LENGTH: 11
<212> TYPE: DNA
<213> ORGANISM: Artificial Sequence

```
<220> FEATURE:
<223> OTHER INFORMATION: Description of Artificial Sequence: variant of
      human pregnane X receptor (hPXR) gene

<400> SEQUENCE: 55
gaggccgaga t                                                              11

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 56
atctcagcct c                                                              11

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 57
gaggctgaga t                                                              11

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 58
ctgaacaagg c                                                              11

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 59
gccttgttca g                                                              11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 60
ctgaaaaagg c                                                              11

<210> SEQ ID NO 61
<211> LENGTH: 11
<212> TYPE: DNA
<213> ORGANISM: Artificial Sequence
<220> FEATURE:
```

-continued

```
<223> OTHER INFORMATION: Description of Artificial Sequence: variant of
      human pregnane X receptor (hPXR) gene

<400> SEQUENCE: 61 gccttttca g                                                          11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 62 ccagggaga a                                                          11

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 63
ttctcccctg g                                                         11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 64
ccaggtgaga a                                                         11

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 65
ttctcacctg g                                                         11

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 66
gactgtggga g                                                         11

<210> SEQ ID NO 67
<211> LENGTH: 11
<212> TYPE: DNA
<213> ORGANISM: Artificial Sequence
<220> FEATURE:
<223> OTHER INFORMATION: Description of Artificial Sequence: variant of
``` human pregnane X receptor (hPXR) gene

<400> SEQUENCE: 67
ctcccacagt c                                                        11

<210> SEQ ID NO 68
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 68
gactggggga g                                                        11

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 69
ctcccccagt c                                                        11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 70 ccccccctgag g                                                       11

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 71
cctcaggggg g                                                        11

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 72 cccccctgagg                                                         10

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

```
<400> SEQUENCE: 73
cctcaggggg                                                              10

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 74
ttctctgtgg t                                                            11

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 75
accacagaga a                                                            11

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 76
ttctccgtgg t                                                            11

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 77
accacggaga a                                                            11

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 78
actgtgagga c                                                            11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene
```

```
<400> SEQUENCE: 79
gtcctcacag t                                                              11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 80
actgtaagga c                                                              11

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 81
gtccttacag t                                                              11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 82
gaaagcccag t                                                              11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 83
actgggcttt c                                                              11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 84
gaaagtccag t                                                              11

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 85
```
actggacttt c                                                                11

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 86
aagtcggagg t                                                                11

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 87
acctccgact t                                                                11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 88
aagtcagagg t                                                                11

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 89
acctctgact t                                                                11

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 90
tgcatccccc c                                                                11

<210> SEQ ID NO 91
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 91

```
gggggggatgc a                                                   11

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 92
tgcattcccc c                                                    11

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 93
gggggaatgc a                                                    11

<210> SEQ ID NO 94
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 94
cggctgaggt g                                                    11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 95
cacctcagcc g                                                    11

<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 96
cggctcaggt g                                                    11

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 97
cacctgagcc g                                                    11
```

<210> SEQ ID NO 98
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 98
gagagcggca t                                                        11

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 99
atgccgctct c                                                        11

<210> SEQ ID NO 100
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 100
gagagtggca t                                                        11

<210> SEQ ID NO 101
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 101
atgccactct c                                                        11

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 102
gtgtgtgcat g                                                        11

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: variant of human pregnane X receptor (hPXR) gene

<400> SEQUENCE: 103
catgcacaca c                                                        11

```
<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 104
gtgtgggcat g                                                              11

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 105
catgcccaca c                                                              11

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 106
tgggagtgca g                                                              11

<210> SEQ ID NO 107
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 107
ctgcactccc a                                                              11

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 108
tgggaatgca g                                                              11

<210> SEQ ID NO 109
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 109
ctgcattccc a                                                              11
```

<210> SEQ ID NO 110
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 110
ctttgacact a                                                        11

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 111
tagtgtcaaa g                                                        11

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 112
ctttggcact a                                                        11

<210> SEQ ID NO 113
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 113
tagtgccaaa g                                                        11

<210> SEQ ID NO 114
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 114
gacactacct t                                                        11

<210> SEQ ID NO 115
<211> LENGTH: 11
<212> TYPE: DNA
<213> ORGANISM: Artificial Sequence
<220> FEATURE:
<223> OTHER INFORMATION: Description of Artificial Sequence: variant of
    human pregnane X receptor (hPXR) gene

<400> SEQUENCE: 115
aaggtagtgt c                                                        11

<210> SEQ ID NO 116

```
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 116
gacaccacct t                                                             11

<210> SEQ ID NO 117
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 117
aaggtggtgt c                                                             11

<210> SEQ ID NO 118
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 118
agtggctgcg a                                                             11

<210> SEQ ID NO 119
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 119
tcgcagccac t                                                             11

<210> SEQ ID NO 120
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 120
agtggttgcg a                                                             11

<210> SEQ ID NO 121
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 121
tcgcaaccac t                                                             11

<210> SEQ ID NO 122
<211> LENGTH: 11
```

```
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 122
agtggcggga a                                                          11

<210> SEQ ID NO 123
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 123
ttcccgccac t                                                          11

<210> SEQ ID NO 124
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 124
agtggtggga a                                                          11

<210> SEQ ID NO 125
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 125
ttcccaccac t                                                          11

<210> SEQ ID NO 126
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 126 aaggggggccg c                                                         11

<210> SEQ ID NO 127
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 127
gcggccccct t                                                          11

<210> SEQ ID NO 128
<211> LENGTH: 11
<212> TYPE: DNA
```

<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 128
aagggagccg c                                                        11

<210> SEQ ID NO 129
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 129
gcggctccct t                                                        11

<210> SEQ ID NO 130
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 130
tggcagggca g                                                        11

<210> SEQ ID NO 131
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 131
ctgccctgcc a                                                        11

<210> SEQ ID NO 132
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 132
tggcaaggca g                                                        11

<210> SEQ ID NO 133
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 133
ctgccttgcc a                                                        11

<210> SEQ ID NO 134
<211> LENGTH: 11
<212> TYPE: DNA
<213> ORGANISM: Artificial Sequence

```
<220> FEATURE:
<223> OTHER INFORMATION: Description of Artificial Sequence: variant of
      human pregnane X receptor (hPXR) gene

<400> SEQUENCE: 134
acaagatatt g                                                            11

<210> SEQ ID NO 135
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 135
caatatcttg t                                                            11

<210> SEQ ID NO 136
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 136
acaaggtatt g                                                            11

<210> SEQ ID NO 137
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 137
caataccttg t                                                            11

<210> SEQ ID NO 138
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 138
tccatcctgt t                                                            11

<210> SEQ ID NO 139
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 139
aacaggatgg a                                                            11

<210> SEQ ID NO 140
<211> LENGTH: 11
<212> TYPE: DNA
<213> ORGANISM: Artificial Sequence
<220> FEATURE:
```

```
<223> OTHER INFORMATION: Description of Artificial Sequence: variant of
      human pregnane X receptor (hPXR) gene

<400> SEQUENCE: 140
tccattctgt t                                                            11

<210> SEQ ID NO 141
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 141
aacagaatgg a                                                            11

<210> SEQ ID NO 142
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 142
cactacatgc t                                                            11

<210> SEQ ID NO 143
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 143
agcatgtagt g                                                            11

<210> SEQ ID NO 144
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 144
cactatatgc t                                                            11

<210> SEQ ID NO 145
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 145
agcatatagt g                                                            11

<210> SEQ ID NO 146
<211> LENGTH: 11
<212> TYPE: DNA
<213> ORGANISM: Artificial Sequence
<220> FEATURE:
<223> OTHER INFORMATION: Description of Artificial Sequence: variant of
```

-continued human pregnane X receptor (hPXR) gene

<400> SEQUENCE: 146 cccccccagcc t                                                             11

<210> SEQ ID NO 147
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 147 aggctgggggg g                                                             11

<210> SEQ ID NO 148
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 148 cccccctagcc t                                                             11

<210> SEQ ID NO 149
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 149
aggctagggg g                                                              11

<210> SEQ ID NO 150
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 150
aattcgccat t                                                              11

<210> SEQ ID NO 151
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 151
aatggcgaat t                                                              11

<210> SEQ ID NO 152
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene -continued

```
<400> SEQUENCE: 152
aattcaccat t                                                              11

<210> SEQ ID NO 153
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 153
aatggtgaat t                                                              11

<210> SEQ ID NO 154
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 154
gtgagggagc c                                                              11

<210> SEQ ID NO 155
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 155
ggctccctca c                                                              11

<210> SEQ ID NO 156
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 156
gtgagagagc c                                                              11

<210> SEQ ID NO 157
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 157
ggctctctca c                                                              11

<210> SEQ ID NO 158
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene
```

```
<400> SEQUENCE: 158
tgagcggctg c                                                    11

<210> SEQ ID NO 159
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 159
gcagccgctc a                                                    11

<210> SEQ ID NO 160
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 160
tgagcagctg c                                                    11

<210> SEQ ID NO 161
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 161
gcagctgctc a                                                    11

<210> SEQ ID NO 162
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 162
cttgggtgac a                                                    11

<210> SEQ ID NO 163
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 163
tgtcacccaa g                                                    11

<210> SEQ ID NO 164
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 164
```

```
cttggatgac a                                                           11
```

<210> SEQ ID NO 165
<211> LENGTH: 11
<212> TYPE: DNA
<213> ORGANISM: Artificial Sequence
<220> FEATURE:
<223> OTHER INFORMATION: Description of Artificial Sequence: variant of
      human pregnane X receptor (hPXR) gene

<400> SEQUENCE: 165

```
tgtcatccaa g                                                           11
```

<210> SEQ ID NO 166
<211> LENGTH: 345
<212> TYPE: DNA
<213> ORGANISM: Homo sapiens
<220> FEATURE:
<221> NAME/KEY: CDS
<222> LOCATION: (83)..(277)

<400> SEQUENCE: 166

```
ctgaggcctc tacacatccc tgtccagtct tttcattctc tgtggttttc tcatttctag       60
tccaagaggc ccagaagcaa ac ctg gag gtg aga ccc aaa gaa agc tgg aac       112
                         Leu Glu Val Arg Pro Lys Glu Ser Trp Asn
                           1               5                  10 cat gct gac ttt gta cac tgt aag gac aca gag tct gtt cct gga aag       160
His Ala Asp Phe Val His Cys Lys Asp Thr Glu Ser Val Pro Gly Lys
             15                  20                  25 ccc agt gtc aac gca gat gag gaa gtc gga ggt ccc caa atc tgc cgt       208
Pro Ser Val Asn Ala Asp Glu Glu Val Gly Gly Pro Gln Ile Cys Arg
         30                  35                  40 gta tgt ggg gac aag gcc act ggc tat cac ttc aat gtc atg aca tgt       256
Val Cys Gly Asp Lys Ala Thr Gly Tyr His Phe Asn Val Met Thr Cys
     45                  50                  55 gaa gga tgc aag ggc ttt ttc aggtagagtt acccatcagc cttcacccac           307
Glu Gly Cys Lys Gly Phe Phe
 60                 65 gtgccaccac tgacccactg ggtaacatct cagggcct                              345
```

<210> SEQ ID NO 167
<211> LENGTH: 65
<212> TYPE: PRT
<213> ORGANISM: Homo sapiens

<400> SEQUENCE: 167

Leu Glu Val Arg Pro Lys Glu Ser Trp Asn His Ala Asp Phe Val His
  1               5                  10                  15

Cys Lys Asp Thr Glu Ser Val Pro Gly Lys Pro Ser Val Asn Ala Asp
             20                  25                  30

Glu Glu Val Gly Gly Pro Gln Ile Cys Arg Val Cys Gly Asp Lys Ala
         35                  40                  45

Thr Gly Tyr His Phe Asn Val Met Thr Cys Glu Gly Cys Lys Gly Phe
     50                  55                  60

Phe
 65

<210> SEQ ID NO 168
<211> LENGTH: 345
<212> TYPE: DNA
<213> ORGANISM: Homo sapiens

```
<220> FEATURE:
<221> NAME/KEY: CDS
<222> LOCATION: (83)..(277)

<400> SEQUENCE: 168
ctgaggcctc tacacatccc tgtccagtct tttcattctc tgtggttttc tcatttctag      60
tccaagaggc ccagaagcaa ac ctg gag gtg aga ccc aaa gaa agc tgg aac     112
                         Leu Glu Val Arg Pro Lys Glu Ser Trp Asn
                          1               5                  10 cat gct gac ttt gta cac tgt gag gac aca gag tct gtt cct gga aag     160
His Ala Asp Phe Val His Cys Glu Asp Thr Glu Ser Val Pro Gly Lys
             15                  20                  25 tcc agt gtc aac gca gat gag gaa gtc gga ggt ccc caa atc tgc cgt     208
Ser Ser Val Asn Ala Asp Glu Glu Val Gly Gly Pro Gln Ile Cys Arg
         30                  35                  40 gta tgt ggg gac aag gcc act ggc tat cac ttc aat gtc atg aca tgt     256
Val Cys Gly Asp Lys Ala Thr Gly Tyr His Phe Asn Val Met Thr Cys
     45                  50                  55 gaa gga tgc aag ggc ttt ttc aggtagagtt acccatcagc cttcacccac         307
Glu Gly Cys Lys Gly Phe Phe
 60                  65 gtgccaccac tgacccactg ggtaacatct cagggcct                            345

<210> SEQ ID NO 169
<211> LENGTH: 65
<212> TYPE: PRT
<213> ORGANISM: Homo sapiens

<400> SEQUENCE: 169

Leu Glu Val Arg Pro Lys Glu Ser Trp Asn His Ala Asp Phe Val His
 1               5                  10                  15

Cys Glu Asp Thr Glu Ser Val Pro Gly Lys Ser Ser Val Asn Ala Asp
                 20                  25                  30

Glu Glu Val Gly Gly Pro Gln Ile Cys Arg Val Cys Gly Asp Lys Ala
             35                  40                  45

Thr Gly Tyr His Phe Asn Val Met Thr Cys Glu Gly Cys Lys Gly Phe
         50                  55                  60

Phe
 65

<210> SEQ ID NO 170
<211> LENGTH: 345
<212> TYPE: DNA
<213> ORGANISM: Homo sapiens
<220> FEATURE:
<221> NAME/KEY: CDS
<222> LOCATION: (83)..(277)

<400> SEQUENCE: 170
ctgaggcctc tacacatccc tgtccagtct tttcattctc tgtggttttc tcatttctag      60
tccaagaggc ccagaagcaa ac ctg gag gtg aga ccc aaa gaa agc tgg aac     112
                         Leu Glu Val Arg Pro Lys Glu Ser Trp Asn
                          1               5                  10 cat gct gac ttt gta cac tgt gag gac aca gag tct gtt cct gga aag     160
His Ala Asp Phe Val His Cys Glu Asp Thr Glu Ser Val Pro Gly Lys
             15                  20                  25 ccc agt gtc aac gca gat gag gaa gtc aga ggt ccc caa atc tgc cgt     208
Pro Ser Val Asn Ala Asp Glu Glu Val Arg Gly Pro Gln Ile Cys Arg
         30                  35                  40 gta tgt ggg gac aag gcc act ggc tat cac ttc aat gtc atg aca tgt     256
```

```
Val Cys Gly Asp Lys Ala Thr Gly Tyr His Phe Asn Val Met Thr Cys
        45                  50                  55 gaa gga tgc aag ggc ttt ttc aggtagagtt acccatcagc cttcacccac        307
Glu Gly Cys Lys Gly Phe Phe
 60                  65 gtgccaccac tgacccactg ggtaacatct cagggcct                           345

<210> SEQ ID NO 171
<211> LENGTH: 65
<212> TYPE: PRT
<213> ORGANISM: Homo sapiens

<400> SEQUENCE: 171

Leu Glu Val Arg Pro Lys Glu Ser Trp Asn His Ala Asp Phe Val His
 1               5                  10                  15

Cys Glu Asp Thr Glu Ser Val Pro Gly Lys Pro Ser Val Asn Ala Asp
                20                  25                  30

Glu Glu Val Arg Gly Pro Gln Ile Cys Arg Val Cys Gly Asp Lys Ala
            35                  40                  45

Thr Gly Tyr His Phe Asn Val Met Thr Cys Glu Gly Cys Lys Gly Phe
        50                  55                  60

Phe
 65

<210> SEQ ID NO 172
<211> LENGTH: 423
<212> TYPE: DNA
<213> ORGANISM: Homo sapiens
<220> FEATURE:
<221> NAME/KEY: CDS
<222> LOCATION: (105)..(290)

<400> SEQUENCE: 172
taacggcttc tgctgccttg agagggttac acagtggctc tccagggggc tggaggctca   60 ccagggcac gtgtgcctga gccagcctca ctgtccctgc agtg atc atg tcc gac    116
                                                 Ile Met Ser Asp
                                                          1 gag gcc gtg gag gag agg cgg gcc ttg atc aag cgg aag aaa agt gaa    164
Glu Ala Val Glu Glu Arg Arg Ala Leu Ile Lys Arg Lys Lys Ser Glu
 5                  10                  15                  20 cgg aca ggg act cag cca ctg gga atg cag ggg ctg aca gag gag cag    212
Arg Thr Gly Thr Gln Pro Leu Gly Met Gln Gly Leu Thr Glu Glu Gln
                25                  30                  35 cgg atg atg atc agg gag ctg atg gac gct cag atg aaa acc ttt gac    260
Arg Met Met Ile Arg Glu Leu Met Asp Ala Gln Met Lys Thr Phe Asp
            40                  45                  50 act acc ttc tcc cat ttc aag aat ttc cgg gtaggaggaa ctgcacagtg       310
Thr Thr Phe Ser His Phe Lys Asn Phe Arg
        55                  60 acccgaggtg tcactgccat cttcattctc acatagaaac tgaggttccc caaggataag   370
aaacttatac aaggtcacag ctaatcagtg gtggagggta gatttggaga gct          423

<210> SEQ ID NO 173
<211> LENGTH: 62
<212> TYPE: PRT
<213> ORGANISM: Homo sapiens

<400> SEQUENCE: 173

Ile Met Ser Asp Glu Ala Val Glu Glu Arg Arg Ala Leu Ile Lys Arg
 1               5                  10                  15
```

-continued

```
Lys Lys Ser Glu Arg Thr Gly Thr Gln Pro Leu Gly Met Gln Gly Leu
             20                  25                  30

Thr Glu Glu Gln Arg Met Met Ile Arg Glu Leu Met Asp Ala Gln Met
         35                  40                  45

Lys Thr Phe Asp Thr Thr Phe Ser His Phe Lys Asn Phe Arg
     50                  55                  60

<210> SEQ ID NO 174
<211> LENGTH: 423
<212> TYPE: DNA
<213> ORGANISM: Homo sapiens
<220> FEATURE:
<221> NAME/KEY: CDS
<222> LOCATION: (105)..(290)

<400> SEQUENCE: 174
taacggcttc tgctgccttg agagggttac acagtggctc tccagggggc tggaggctca      60 ccagggcac gtgtgcctga gccagcctca ctgtccctgc agtg atc atg tcc gac       116
                                            Ile Met Ser Asp
                                              1 gag gcc gtg gag gag agg cgg gcc ttg atc aag cgg aag aaa agt gaa      164
Glu Ala Val Glu Glu Arg Arg Ala Leu Ile Lys Arg Lys Lys Ser Glu
  5                  10                  15                  20 cgg aca ggg act cag cca ctg gga gtg cag ggg ctg aca gag gag cag      212
Arg Thr Gly Thr Gln Pro Leu Gly Val Gln Gly Leu Thr Glu Glu Gln
             25                  30                  35 cgg atg atg atc agg gag ctg atg gac gct cag atg aaa acc ttt ggc      260
Arg Met Met Ile Arg Glu Leu Met Asp Ala Gln Met Lys Thr Phe Gly
         40                  45                  50 act acc ttc tcc cat ttc aag aat ttc cgg gtaggaggaa ctgcacagtg        310
Thr Thr Phe Ser His Phe Lys Asn Phe Arg
     55                  60 acccgaggtg tcactgccat cttcattctc acatagaaac tgaggttccc caaggataag     370
aaacttatac aaggtcacag ctaatcagtg gtggagggta gatttggaga gct           423

<210> SEQ ID NO 175
<211> LENGTH: 62
<212> TYPE: PRT
<213> ORGANISM: Homo sapiens

<400> SEQUENCE: 175

Ile Met Ser Asp Glu Ala Val Glu Glu Arg Arg Ala Leu Ile Lys Arg
  1               5                  10                  15

Lys Lys Ser Glu Arg Thr Gly Thr Gln Pro Leu Gly Val Gln Gly Leu
             20                  25                  30

Thr Glu Glu Gln Arg Met Met Ile Arg Glu Leu Met Asp Ala Gln Met
         35                  40                  45

Lys Thr Phe Gly Thr Thr Phe Ser His Phe Lys Asn Phe Arg
     50                  55                  60

<210> SEQ ID NO 176
<211> LENGTH: 271
<212> TYPE: DNA
<213> ORGANISM: Homo sapiens
<220> FEATURE:
<221> NAME/KEY: CDS
<222> LOCATION: (80)..(181)

<400> SEQUENCE: 176
gagcaatgcc ctgactctgg gctggactga gcttgtcttt gccccatgat cttgcaccac      60
```

```
acctccctcc cctccagac cgc cca ggt gtg ctg cag cac cgc gtg gtg gac      112
                    Arg Pro Gly Val Leu Gln His Arg Val Val Asp
                     1               5                  10 cag ctg cag gag caa ttc acc att act ctg aag tcc tac att gaa tgc      160
Gln Leu Gln Glu Gln Phe Thr Ile Thr Leu Lys Ser Tyr Ile Glu Cys
             15                  20                  25 aat cgg ccc cag cct gct cat aggtgagcac agcaggggt gaggacccgt          211
Asn Arg Pro Gln Pro Ala His
             30 gagggtgatg tgagggagcc gaggttcagg gaaattgccc aagacttcat ggccagaggg    271
```

<210> SEQ ID NO 177
<211> LENGTH: 34
<212> TYPE: PRT
<213> ORGANISM: Homo sapiens

<400> SEQUENCE: 177

```
Arg Pro Gly Val Leu Gln His Arg Val Val Asp Gln Leu Gln Glu Gln
 1               5                  10                  15

Phe Thr Ile Thr Leu Lys Ser Tyr Ile Glu Cys Asn Arg Pro Gln Pro
            20                  25                  30

Ala His
```

<210> SEQ ID NO 178
<211> LENGTH: 962
<212> TYPE: DNA
<213> ORGANISM: Homo sapiens
<220> FEATURE:
<223> OTHER INFORMATION: r=g or a, m=c or a, k=g or t, n=c or deleted

<400> SEQUENCE: 178

```
tcaagtgctg gacttgggac ttaggagggg caatggagcc gcttagtgcc tacatctgac     60
ttggactgaa atataggtga gagacaagat tgtctcatat ccggggaaat cataacctat    120
gactaggacg ggaagaggaa gcactgcctt tacttcagtg gaatctcrg cctcagcctg    180
caagccaagt gttcacagtg aaaaaagcaa gagaataagc taatactcct gtcctgaama   240
aggcagcggc tccttggtaa agctactcct tgatcgatcc tttgcaccgg attgttcaaa   300
gtggacccca ggkgagaagt cggagcaaag aacttaccac caagcaggta tggtttttct   360
ttctttctct tttgctgggg gctgaccgcc cttcagctcc agccaaaaga tgtgtgtgaa   420
cacaaatata ccttctgttt gaggtcagca tcatagtggg tcgtgaatca tgttggcctt   480
gctgctgtct cctcatttct agggtgaaaa aaaaaaagca tgaaaacaat cacttaatgt   540
tgagccccat tactgatgct ctctggtcct gcactagcct cctagaaaaa tcaccacagc   600
cttaactact gcatgagtta ccacaagtca cacatacaac cagctccctg ttacagggct   660
ggagtccctg gacccaggaa ataccacctc caaggactgk gggagctggg gactatggga   720
actgggatca actcagtcct gattccttt ggcctgctgg gttagtgctg gcagccccn    780
tgaggccaag acagcagca tgacagtcac caggactcac cacttcaagg agggtccct   840
cagagcacct gccatacccc tgcacagtgc tgcggctgag ttggcttcaa accagtgagt   900
tttctacctc tactattgaa agggcacctt gtcccacaga accgagtctt gcctgcatgt   960
gg                                                                  962
```

<210> SEQ ID NO 179
<211> LENGTH: 345
<212> TYPE: DNA

```
<213> ORGANISM: Homo sapiens
<220> FEATURE:
<223> OTHER INFORMATION: y=c or t, r=g or a

<400> SEQUENCE: 179
ctgaggcctc tacacatccc tgtccagtct tttcattctc ygtggttttc tcatttctag    60
tccaagaggc ccagaagcaa acctggaggt gagacccaaa gaaagctgga accatgctga   120 cttttgtacac tgtraggaca cagagtctgt tcctggaaag yccagtgtca acgcagatga  180
ggaagtcrga ggtccccaaa tctgccgtgt atgtggggac aaggccactg gctatcactt   240
caatgtcatg acatgtgaag gatgcaaggg cttttttcagg tagagttacc catcagcctt  300
cacccacgtg ccaccactga cccactgggt aacatctcag ggcct                   345

<210> SEQ ID NO 180
<211> LENGTH: 417
<212> TYPE: DNA
<213> ORGANISM: Homo sapiens
<220> FEATURE:
<223> OTHER INFORMATION: y=c or t, s=g or c, k=g or t

<400> SEQUENCE: 180
ctgggacgca aaggctagtg tcccctccc cgagtcggta ggggctgggg agggaggtgg     60
tatggcccgg agcccaggc cgagggcccg ggcaccgtg catycccct tctgctcccc      120 attctctcac aggagggcca tgaaacgcaa cgcccggcts aggtgcccct tccggaaggg   180
cgcctgcgag atcacccgga agacccggcg acagtgccag gcctgccgcc tgcgcaagtg   240
cctggagagy ggcatgaaga aggagagtga gcagtgggcg cgcgggcggg ccggcgccgg   300
ggtgcacggc tctgagtaag gacgtgccgt gggtgtgkgc atgcttgtgt ggagatgcgc   360
gccgagtgtg cgcgtgaaca cacgtgcaca tgtgagctgg tgtccgtgtg caacagg      417

<210> SEQ ID NO 181
<211> LENGTH: 423
<212> TYPE: DNA
<213> ORGANISM: Homo sapiens
<220> FEATURE:
<223> OTHER INFORMATION: r=g or a, y=c or t

<400> SEQUENCE: 181
taacggcttc tgctgccttg agagggttac acagtggctc tccagggggc tggaggctca    60
ccaggggcac gtgtgcctga gccagcctca ctgtccctgc agtgatcatg tccgacgagg   120
ccgtggagga gaggcgggcc ttgatcaagc ggaagaaaag tgaacggaca gggactcagc   180
cactgggart gcagggggctg acagaggagc agcggatgat gatcagggag ctgatggacg   240
ctcagatgaa aacctttgrc acyaccttct cccatttcaa gaatttccgg gtaggaggaa   300
ctgcacagtg acccgaggtg tcactgccat cttcattctc acatagaaac tgaggttccc   360
caaggataag aaacttatac aaggtcacag ctaatcagtg gtgagggta gatttggaga   420 gct                                                                 423

<210> SEQ ID NO 182
<211> LENGTH: 415
<212> TYPE: DNA
<213> ORGANISM: Homo sapiens
<220> FEATURE:
<223> OTHER INFORMATION: y=c or t

<400> SEQUENCE: 182
ctgagttggg acctgtctat gaaagcacat gctgtctctc ctctgtccac ctcctggcat    60
```

-continued

```
gtgtcctagc tgccaggggt gcttagcagt ggytgcgagt tgccagagtc tctgcaggcc    120
ccatcgaggg aagaagctgc caagtggagc caggtccgga aagatctgtg ctctttgaag    180
gtctctctgc agctgcgggg ggaggatggc agtgtctgga actacaaacc cccagccgac    240
agtggyggga aagagatctt ctccctgctg ccccacatgg ctgacatgtc aacctacatg    300

ttcaaaggca tcatcagctt tgccaaagtc atctcctact tcaggtagga catggagact    360
gggtggttgg gtgtggaaaa gaactggaag tggccaggag gttcaaaggg cctgg         415
```

<210> SEQ ID NO 183
<211> LENGTH: 598
<212> TYPE: DNA
<213> ORGANISM: Homo sapiens
<220> FEATURE:
<223> OTHER INFORMATION: r=g or a, y=c or t

<400> SEQUENCE: 183

```
ctgctggtgc cggcctgtgg gctgcctccc agggagctgt cctcccctcc ccatccttgc     60
tgccagggac ttgcccatcg aggaccagat ctccctgctg aagggrgccg ctttcgagct    120
gtgtcaactg agattcaaca cagtgttcaa cgcggagact ggaacctggg agtgtggccg    180
gctgtcctac tgcttggaag acactgcagg tgcccgagag agcctgcctg ccctggcaga    240
gggagggaaa cactgcagtt atgggaggaa gggagctacg ccaggatatg caggttctgg    300
gatggcargg caggaagatg gaatggtgga aaacaagrta ttggtgaggg atgattagat    360
cttggtcagc ttgctgagaa gctgcccctc catyctgtta ccatccacag gtggcttcca    420
gcaacttcta ctggagccca tgctgaaatt ccactayatg ctgaagaagc tgcagctgca    480
tgaggaggag tatgtgctga tgcaggccat ctccctcttc tccccaggtg aggatctccc    540
ctaggctgcc tgacatcccc ccyagcctta tctgccctcc ccagggaagg tcccagtc      598
```

<210> SEQ ID NO 184
<211> LENGTH: 271
<212> TYPE: DNA
<213> ORGANISM: Homo sapiens
<220> FEATURE:
<223> OTHER INFORMATION: r=g or a

<400> SEQUENCE: 184

```
gagcaatgcc ctgactctgg gctggactga gcttgtcttt gccccatgat cttgcaccac     60
acctccctcc cctccagacc gcccaggtgt gctgcagcac cgcgtggtgg accagctgca    120
ggagcaattc rccattactc tgaagtccta cattgaatgc aatcggcccc agcctgctca    180
taggtgagca cagcaggggg tgaggacccg tgagggtgat gtgagrgagc cgaggttcag    240
ggaaattgcc caagacttca tggccagagg g                                   271
```

<210> SEQ ID NO 185
<211> LENGTH: 324
<212> TYPE: DNA
<213> ORGANISM: Homo sapiens
<220> FEATURE:
<223> OTHER INFORMATION: r=g or a

<400> SEQUENCE: 185

```
tgcttgtgca gcctcagagc agccctgagg cttgtgggtc agggcgggct gcacccacaa     60
tcttttctct ggctggcatg caggttcttg ttcctgaaga tcatggctat gctcaccgag    120
ctccgcagca tcaatgctca gcacacccag cggctgctgc gcatccagga catacacccc    180
```

```
tttgctacgc ccctcatgca ggagttgttc ggcatcacag gtagctgagc rgctgccctt      240
ggrtgacacc tccgagaggc agccagaccc agagccctct gagccgccac tcccgggcca      300
agacagatgg acactgccaa gagc                                             324
```